US012708732B2

(12) United States Patent
Bougatef

(10) Patent No.: US 12,708,732 B2
(45) Date of Patent: Aug. 18, 2026

(54) METHOD AND APPARATUS FOR PROVIDING PERCUSSIVE VENTILATION THERAPY TO A PATIENT AIRWAY

(71) Applicant: CircuitLife, LLC, San Antonio, TX (US)

(72) Inventor: Adel Bougatef, San Antonio, TX (US)

(73) Assignee: CircuitLife, LLC, San Antonio, TX (US)

( * ) Notice: Subject to any disclaimer, the term of this patent is extended or adjusted under 35 U.S.C. 154(b) by 1268 days.

(21) Appl. No.: 17/212,571

(22) Filed: Mar. 25, 2021

(65) Prior Publication Data

US 2021/0205567 A1 Jul. 8, 2021

Related U.S. Application Data

(63) Continuation-in-part of application No. 15/656,818, filed on Jul. 21, 2017, now Pat. No. 10,987,274.

(Continued)

(51) Int. Cl.

*A61M 16/12* (2006.01)
*A61M 16/00* (2006.01)
*A61M 16/20* (2006.01)

(52) U.S. Cl.

CPC ...... *A61M 16/127* (2014.02); *A61M 16/0012* (2014.02); *A61M 16/0096* (2013.01); *A61M 16/204* (2014.02); *A61M 16/205* (2014.02)

(58) Field of Classification Search

CPC ............ A61M 15/0021; A61M 16/127; A61M 16/0021; A61M 16/0096; A61M 16/204;

(Continued)

(56) References Cited

U.S. PATENT DOCUMENTS 3,537,448 A 11/1970 Liston
4,118,611 A 10/1978 Harris (Continued)

FOREIGN PATENT DOCUMENTS

CN 102316936 A 1/2012
CN 104334080 A 2/2015

(Continued)

OTHER PUBLICATIONS

Transmittal; International Search Report; and Written Opinion of the International Searching Authority for International Application No. PCT/US2017/043354, with a mailing date of Oct. 25, 2017.

(Continued)

*Primary Examiner* — Brandy S Lee

(74) *Attorney, Agent, or Firm* — Dykema Gossett PLLC

(57) ABSTRACT

Method and apparatus for providing percussive ventilation therapy to a patient airway preferably includes at least one driver unit configured to provide pressurized, non-pulsate gas. At least one patient interface device preferably has structure configured to (i) receive the pressurized, non-pulsate gas from the at least one driver unit and transform it into a pulsed and pressurized gas, and (ii) supply at least one sub tidal volume of pulsed and pressurized gas to a patient through a patient connection orifice. At least one flexible tube is preferably configured to provide pressurized, non-pulsate gas from the at least one driver unit to the at least one patient interface device. Preferably, at least one portion of the patient interface device is disposable, and another portion may be reusable. Preferably, the invention uses Adaptive Dynamic Subtidal Ventilation technology.

19 Claims, 24 Drawing Sheets

Related U.S. Application Data

(60) Provisional application No. 62/369,954, filed on Aug. 2, 2016.

(58) Field of Classification Search
CPC .............. A61M 16/205; A61M 16/201; A61M 16/202; A61M 11/005; A61M 11/06; A24F 7/00
See application file for complete search history.

(56) References Cited

U.S. PATENT DOCUMENTS

| | | | | |
|---|---|---|---|---|
| 4,197,843 | A | 4/1980 | Bird | |
| 4,592,349 | A | 6/1986 | Bird | |
| 4,838,260 | A * | 6/1989 | Bird | A61M 16/0012 128/205.24 |
| 5,862,802 | A | 1/1999 | Bird | |
| 6,581,600 | B2 | 6/2003 | Bird | |
| 6,595,203 | B1 * | 7/2003 | Bird | A61M 16/0006 239/338 |
| 7,011,091 | B2 | 3/2006 | Hill et al. | |
| 7,191,780 | B2 | 3/2007 | Faram | |
| 7,779,841 | B2 | 8/2010 | Dunsmore et al. | |
| 8,025,054 | B2 | 9/2011 | Dunsmore et al. | |
| 8,051,854 | B2 | 11/2011 | Faram | |
| 8,347,883 | B2 | 1/2013 | Bird | |
| 8,365,727 | B2 | 2/2013 | Dunsmore et al. | |
| 8,528,547 | B2 * | 9/2013 | Dunsmore | A61M 11/06 128/203.12 |
| 2002/0162553 | A1 * | 11/2002 | Hamilton | A61M 16/209 128/205.24 |
| 2005/0061318 | A1 | 3/2005 | Faram | |
| 2005/0115566 | A1 | 6/2005 | Van den Akker et al. | |
| 2008/0066754 | A1 | 3/2008 | Faram | |
| 2009/0126731 | A1 | 5/2009 | Dunsmore et al. | |
| 2010/0125227 | A1 * | 5/2010 | Bird | A61M 16/021 128/200.14 |
| 2011/0220107 | A1 | 9/2011 | Gardner et al. | |
| 2012/0318261 | A1 | 12/2012 | Newhouse et al. | |
| 2015/0096562 | A1 * | 4/2015 | Dunsmore | A61M 16/0012 128/203.12 |

FOREIGN PATENT DOCUMENTS

| | | | |
|---|---|---|---|
| WO | 2008/063966 | A1 | 5/2008 |
| WO | 2009067554 | A1 | 5/2009 |
| WO | 2013/068918 | A1 | 5/2013 |
| WO | 2018026549 | A1 | 2/2018 |

OTHER PUBLICATIONS

International Search Report and Written Opinion mailed Jun. 7, 2022, from International Application No. PCT/US2022/020855, 7 sheets.

Notice of Allowance dated Feb. 17, 2021, from U.S. Appl. No. 15/656,818, 7 sheets.

Notice of Allowance dated Dec. 24, 2020, from U.S. Appl. No. 15/656,818, 25 sheets.

Final Rejection dated Aug. 5, 2020, from U.S. Appl. No. 15/656,818, 22 sheets.

Non-Final Rejection dated Mar. 19, 2020, from U.S. Appl. No. 15/656,818, 32 sheets.

Chinese Office Action dated Jan. 4, 2021, from Chinese Patent Application No. 201780061035.8, 9 sheets.

Communication pursuant to Article 94(3) EPC dated Aug. 1, 2025, from European Patent Application No. 22715279.0, 4 sheets.

* cited by examiner

HOMECARE / THERAPY DEVICES (Wireless connection version)

HOMECARE / THERAPY DEVICES

METHOD AND APPARATUS FOR PROVIDING PERCUSSIVE VENTILATION THERAPY TO A PATIENT AIRWAY

CROSS REFERENCE TO RELATED APPLICATIONS

This application is a continuation-in-part (CIP) application of U.S. application Ser. No. 15/656,818, filed on Jul. 21, 2017, which claims priority to U.S. Provisional Patent Appin. No. 62/369,954, filed Aug. 2, 2016, the entire contents of which are incorporated herein by reference.

BACKGROUND OF THE INVENTION

The respiratory airways employ tiny hairs, called motile cilia, which beat in coordinated waves to facilitate removal of pulmonary mucus by directing it to the back of the throat. Illness such as Chronic Obstructive Pulmonary Disease (COPD) are indications of damage to the respiratory surfaces, causing inflammation (which affect the cilia's ability to mobilize secretions), increased mucus production, and swollen passageways which restrict airflow, further reducing the body's ability to remove mucus.

With the ageing populations, the prevalence of lung disease is increasing, particularly in those countries with a high smoking incidence.

Acute and chronic lung diseases management remains an important health problem with substantial mortality and morbidity. Beside smoking, infections and pollution, other factors as population density and urbanization, migration and global travel, can lead to the increase in the prevalence of lung diseases.

Ventilators that supply small bursts of high frequency air pulses are becoming increasingly recognized as an effective therapeutic treatment to facilitate alveoli recruitment (hence lung volume) and aid in the removal of mucus secretions from the lung. The pulses of air provide kinetic energy to the air column within the patient's airway without triggering the Hering-Breuer pulmonary stretch reflex, and provide an average positive airway pressure (PAP) effect. The average positive airway pressure and oscillating column of air help mobilize mucus, especially when combined with medicated aerosols, although the exact mechanism of operation is not known.

Unfortunately, there are few effective devices able to deliver percussive ventilation therapy, and those which are proven effective are expensive.

U.S. Pat. No. 4,592,349 discloses a distal (to the patient) Driver Unit which comprises a pressure reduction regulator and pneumatic oscillating air interrupter valve to supply pulses of air via a hose to a proximal Patient Interface Device, which comprises a sliding Venturi mechanism to provide an enhanced percussive effect. However, the Driver Unit employs a pneumatic air interrupter valve which requires high pressure (up to 40 psi) to reliably provide a high-frequency percussive effect, resulting in a large, noisy Driver unit that is power inefficient, must be operated from mains, and is costly to manufacture.

U.S. Pat. No. 7,191,780 discloses a low cost apparatus for delivering high frequency pulses of air to a patient. This includes a distal Driver Unit which comprises a pressure reduction regulator to stabilize a source of compressed air, and configurable flow interrupter valve which supplies pulses of air via a hose to a proximal Patient Interface Device.

U.S. Pat. No. 8,365,727 discloses a distal base unit comprising at least one electronic air interrupter valve, which may be supplied from a compressed air source and pressure reduction regulator within the Driver unit, or may be supplied from a regulated pressure source e.g. from hospital air supply outlet. The Driver unit outlet then supplies a proximal Patient Interface Device with pulses of air via a hose.

However, any approach to generate percussive ventilation which employs an air interrupter valve in a distal Driver feeding pulses of air to a proximal Patient Interface Device will suffer from lessening of the percussive effect caused by both the compressibility and inertia of the air contained within the hose from the distal Driver unit to the Patient Interface Device, and also dampening effects due to the elastic compliance of the hose itself. In addition, the air interrupter valve must endure millions of cycles of operation during the Driver unit lifetime, is prone to wear and requires expensive maintenance to replace.

U.S. Pat. No. 4,592,349 additionally discloses how to enhance damped percussive pulses by employing an air operated servo assisted sliding Venturi shuttle to enhance percussive pressure pulse waveforms applied to the patient. However, as in the case of the pneumatic air interrupter valve, but also this requires high working pressure in the Driver Unit (up to 40 psi, with associated bulk, noise, and low efficiency), whereas the jet pressure applied to the Venturi inlet is typically less than 10 psi. In addition, the sliding Venturi shuttle is only activated in one direction, whereas double acting sliding Venturi shuttle will improve the sharpness of pressure waveforms applied to the patient's pulmonary airway, and hence improve the percussive effect.

In light of this, a need exists for a low cost, low power, low noise, efficacious percussive therapy system which operates in conjunction with a low cost Patient Interface Device.

SUMMARY OF THE INVENTION

The present invention provides an effective system and method for facilitating mobilization of mucus using percussive ventilations, with reduced complexity and hence lower cost. It comprises a source of pressurized gas from a Driver unit which is supplied at constant pressure to a Patient Interface Device. The Patient Interface Device preferably comprises a disposable part and reusable part: the reusable part preferably employs an air interrupter valve and the disposable part preferably employs a Venturi system.

The present invention also provides an effective system and method for protecting injured lungs using Adaptive Dynamic Subtidal ventilation (ADSV technology; see definition below). It preferably comprises a source of pressurized gas from a Driver unit, which is supplied at constant pressure to a Patient Interface Device. The Patient Interface Device preferably comprises a disposable part and reusable part: the reusable part preferably employs a gas interrupter valve and the disposable part preferably employs a sliding Venturi system.

An object of the invention is to preferably provide an efficacious, continuous, high frequency percussive breathing therapy that does not rely on expensive consumables. Another object of the invention is to preferably reduce the bulk, noise, and complexity of the Driver unit to lower manufacturing costs. Yet another object of the invention is to preferably reduce the power consumption of the system to permit convenient transport and battery powered operation. A further object of the invention is to preferably lower maintenance and service costs. Another object of the invention is to preferably provide a simple, convenient, and easy to use system.

Another object of the invention is to preferably provide an efficacious, continuous, Adaptive Dynamic Subtidal ventilation therapy. Another object of the invention is to preferably reduce the bulk, noise, and reduce the power consumption of the system to permit convenient transport and battery powered operation. A further object of the invention is to preferably lower maintenance and service costs. Another object of the invention is to preferably provide a simple, convenient, and easy to use system.

According to a first aspect of the present invention, apparatus for delivering percussive air pulses to a patient preferably has at least one Driver unit configured to provide pressurized, non-pulsate gas. At least one patient interface device preferably has structure configured to (i) receive the pressurized, non-pulsate gas from the driver unit and transform it into a pulsed and pressurized gas, and (ii) supply at least one sub tidal volume of pulsed and pressurized gas to a patient through a patient connection orifice. At least one flexible tube is preferably configured to provide pressurized, non-pulsate gas from the at least one driver unit to the at least one patient interface device. Preferably, the at least one flexible tube has a length of from 1-7 feet.

According to a second aspect of the present invention, a patient interface device for delivering percussive air pulses to a patient through a patient connection orifice preferably has at least one gas inlet configured to receive pressurized, non-pulsate gas. At least one gas interrupter valve is preferably configured to receive the pressurized, non-pulsate gas from the driver unit and transform it into a pulsed and pressurized gas. At least one Venturi valve is preferably configured to (i) receive the pulsed and pressurized gas stream from the at least one gas interrupter valve, (ii) transform the pulsed and pressurized gas into at least one sub tidal volume of pulsed and pressurized gas, and (iii) deliver the at least one sub tidal volume of pulsed and pressurized gas to the patient connection orifice.

According to a third aspect of the present invention, a driver unit for percussive patient treatment preferably has at least one gas inlet configured to provide at least one pressurized, non-pulsate gas to at least one pressure vessel. The at least one pressure vessel is preferably configured to store the at least one pressurized, non-pulsate gas. At least one gas outlet is preferably configured to output the stored at least one pressurized, non-pulsate gas from the driver unit. At least one electronic controller is preferably configured to (i) receive signals from at least one patient interface device, and (ii) control operation of the at least one pressure vessel.

According to a fourth aspect of the present invention, apparatus using ADSV technology to ventilate a patient preferably has at least one Driver unit configured to provide pressurized, non-pulsate gas. At least one patient interface device preferably has structure configured to (i) receive the pressurized, non-pulsate gas from the driver unit and transform it into a pulsed and pressurized gas, and (ii) supply at least one sub tidal volume of pulsed and pressurized gas to a patient through a patient connection orifice. At least one flexible tube is preferably configured to provide pressurized, non-pulsate gas from the at least one driver unit to the at least one patient interface device. Preferably, the at least one flexible tube has a length of from 1-7 feet.

According to a fifth aspect of the present invention, a patient interface device using ADSV technology to ventilate a patient through a patient connection orifice preferably has at least one gas inlet configured to receive pressurized, non-pulsate gas. At least one gas interrupter valve is preferably configured to receive the pressurized, non-pulsate gas from the driver unit and transform it into a pulsed and pressurized gas. At least one sliding Venturi valve is preferably configured to (i) receive the pulsed and pressurized gas stream from the at least one gas interrupter valve, (ii) transform the pulsed and pressurized gas into at least one sub tidal volume of pulsed and pressurized gas, (iii) deliver the at least one sub tidal volume of pulsed and pressurized gas to the patient connection orifice, and (iv) operate as inspiratory, expiratory valves all in one, that means, each sub tidal delivered will be followed by one subtidal volume exhaled.

According to a sixth aspect of the present invention, a driver unit using ADSV technology for patient treatment preferably has at least one gas inlet configured to provide at least one pressurized, non-pulsate gas to at least one pressure vessel. The at least one pressure vessel is preferably configured to store the at least one pressurized, non-pulsate gas. At least one gas outlet is preferably configured to output the stored at least one pressurized, non-pulsate gas from the driver unit. At least one electronic controller is preferably configured to (i) receive signals from at least one patient interface device, and (ii) control operation of the at least one pressure vessel.

BRIEF DESCRIPTION OF THE DRAWINGS

Exemplary embodiments of the presently preferred features of the present invention will now be described with reference to the accompanying drawings.

FIGS. 7*a*, 7*b*, 7*c*, and 7*d* are schematic perspective views of a Patient Interface Device Connector for attachment to the Patient Interface Device according to the FIGS. 1-3 embodiments; wherein FIG. 7*a* is a back perspective view, FIG. 7*b* is a front perspective view, FIG. 7*c* is a front plan view, and FIG. 7*d* is a side plan view.

DETAILED DESCRIPTION

In overview, the present embodiments provide a Home Therapy and/or Hospital Therapy apparatus and method whereby percussive ventilation therapy is provided to at least one patient's airway. While the present invention has particular applicability to human patients, the preferred embodiments may be of use to any animal patient(s) as well.

"Adaptive Dynamic Subtidal Ventilation" (ADSV) technology in this specification may include, but is not limited to, one or more of, or any combination of structure and/or function whereby the Patient Interface Device is: Adaptive because the delivered flow will permanently adapt to patient physiologic parameters; Dynamic because it will have a waveform that brings energy to recruit the airways and will affect the hemodynamic (the permanent change in flow/pressure/volume is dynamic); Subtidal because it will deliver small volumes called subtidal volumes; and Ventilation because it will affect gas exchange, oxygenate, and ventilate.

A "controller" in this specification may include, but is not limited to, one or more of, or any combination of processing device(s) which run one or more stored "computer programs" and/or non-transitory "computer-readable media" to cause the device(s) and/or unit(s) to perform the functions recited herein. The media may include Compact Discs, DVDs, ROM, RAM, solid-state memory, or any other storage device capable of storing the one or more computer programs.

The term "processor" as used herein means processing devices, apparatus, programs, circuits, components, systems, and subsystems, whether implemented in hardware, tangibly-embodied software or both, and whether or not programmable. The term "processor" as used herein includes, but is not limited to, one or more computers, hardwired circuits, signal modifying devices and systems, devices, and machines for controlling systems, central processing units, programmable devices, and systems, field-programmable gate arrays, application-specific integrated circuits, systems on a chip, systems comprised of discrete elements and/or circuits, state machines, virtual machines, data processors, processing facilities, and combinations of any of the foregoing.

The terms "storage" and "data storage" and "memory" as used herein mean one or more data storage devices, apparatus, programs, circuits, components, systems, subsystems, locations, and storage media serving to retain data, whether on a temporary or permanent basis, and to provide such retained data. The terms "storage" and "data storage" and "memory" as used herein include, but are not limited to, hard disks, solid state drives, flash memory, DRAM, RAM, ROM, tape cartridges, and any other medium capable of storing computer-readable data.

Figure 1:
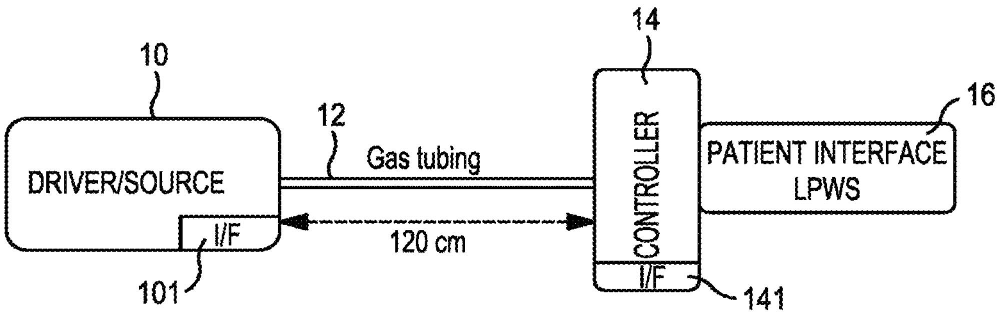
FIG. 1 is a schematic block diagram of a Homecare/Therapy embodiment according to the present invention, featuring a wireless connection between the Driver Unit and the Patient Interface Device.
Figure 2:
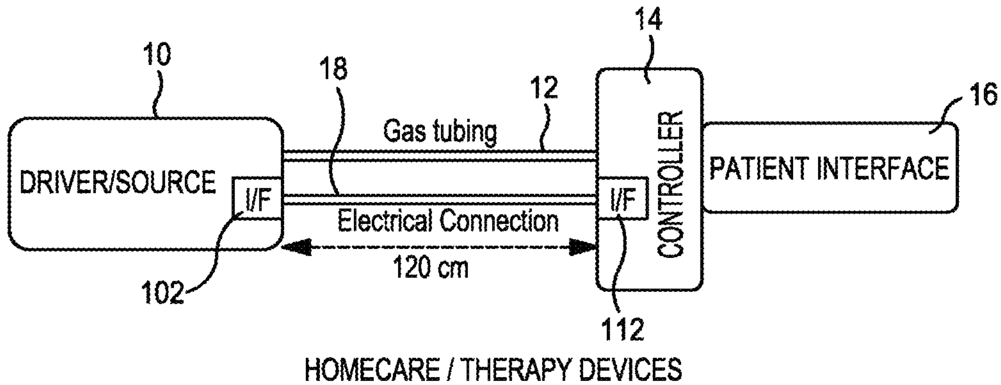
FIG. 2 is a schematic block diagram of a Homecare/Therapy embodiment according to the present invention, featuring a wired connection between the Driver Unit and the Patient Interface Device.

FIGS. 1 and 2 depict a Homecare/Therapy embodiment according to the present invention. In FIG. 1, a Driver/source unit 10 is preferably coupled to a Patient Interface Device 16 via gas tubing 12 and a controller 14. Preferably, the gas tubing 12 preferably comprises low compliance single-lumen plastic tubing approximately 120 cm (about 48 inches or 4 feet). Of course, the length of the tubing 12 may be any convenient or desirable length, such as 2, 3, 4, 5, 6, 7, 8, 9, 10, 11, 12 feet, or any range of feet noted above, such as 1-7 feet, 2-6 feet, 3-5 feet, or larger; the tubing 12 may also be stretchable, as with common vacuum hoses. In this embodiment, the Driver Unit 10 preferably has a low power wireless interface 101 that is coupled to the controller 14 via another low power wireless interface 141. Of course, the power levels of these interfaces may be adjusted according to the local electrical environment. In FIG. 2, the Driver Unit has a wired interface 102 that is coupled, via wiring 18, to an interface 142 of the controller 14.

Figure 3:
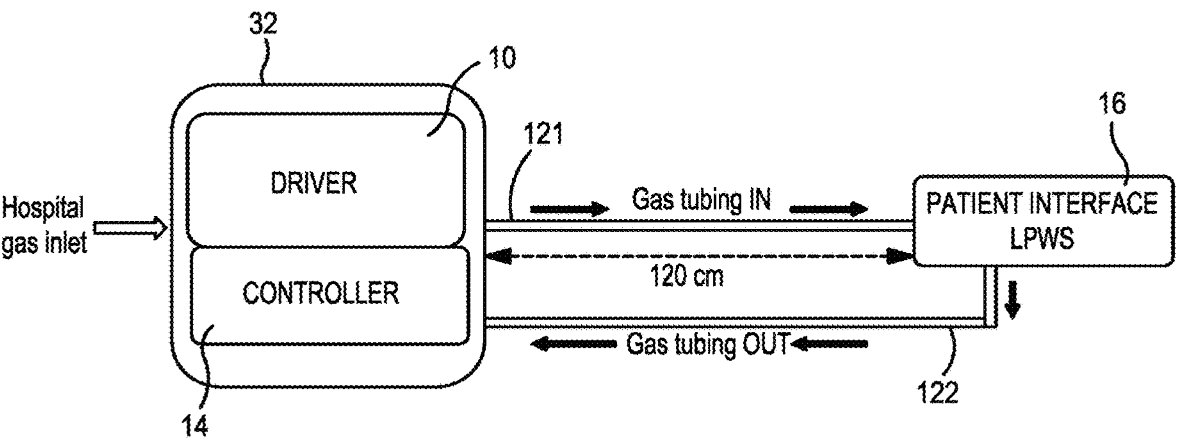
FIG. 3 is a schematic block diagram of a Hospital Continuous Ventilation embodiment according to the present invention, featuring a wireless connection between the Driver Unit and the Patient Interface Device.

FIG. 3 depicts a Hospital Continuous Ventilation embodiment according to the present invention. In FIG. 3, the controller 14 may be disposed adjacent to (or even within) the Driver 10, and is preferably disposed within a hospital enclosure 32, rather than adjacent the Patient Interface Device as in FIGS. 1 and 2.

Driver Unit.

Figure 4:
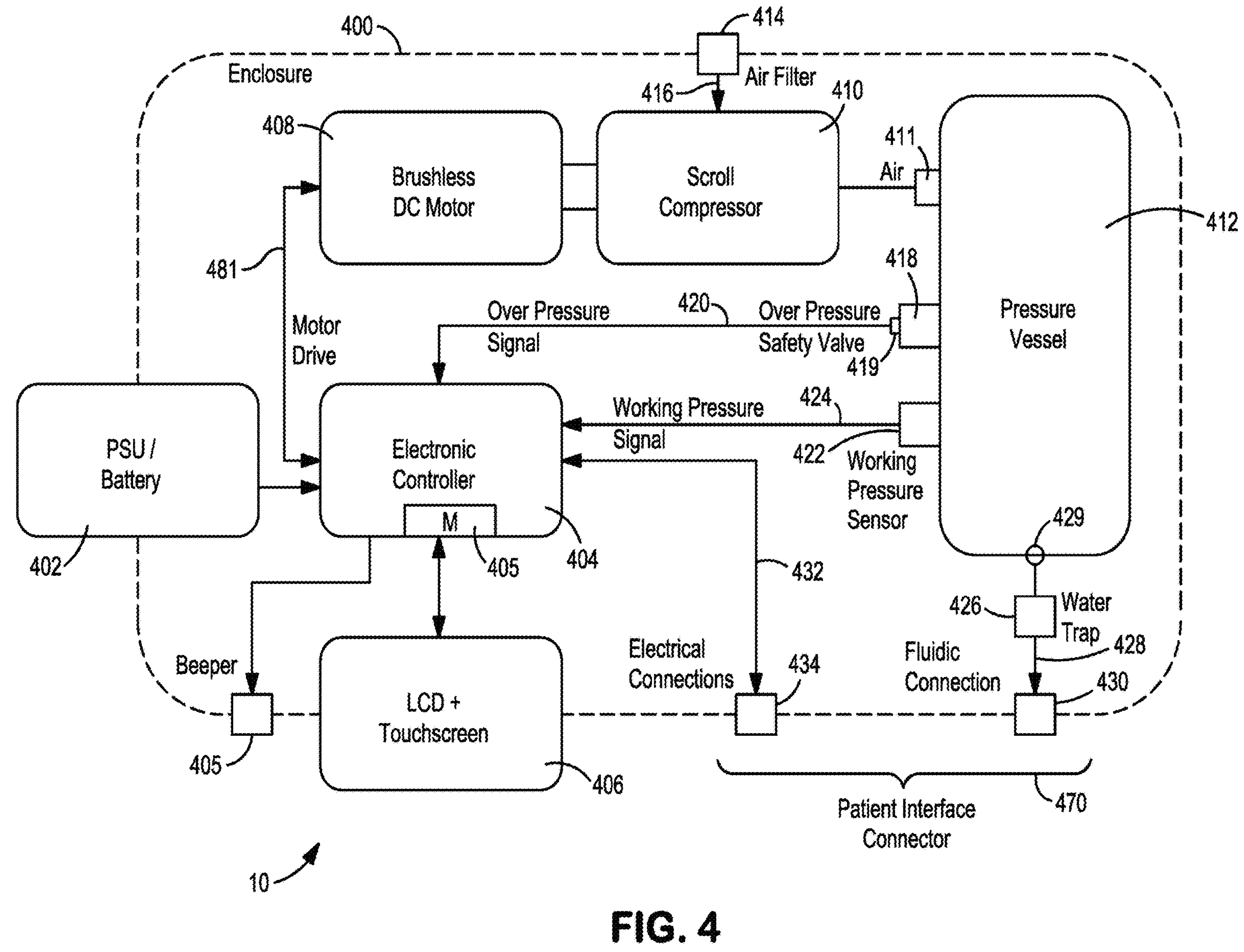
FIG. 4 is a schematic block diagram of an embodiment of the Driver Unit according to the FIG. 1 embodiment.

FIG. 4 shows the major components of the Driver Unit 10 according to the FIG. 1 (Home Therapy) embodiment, preferably contained within a plastic or metal enclosure 400. A Power Supply Unit (PSU)/Battery 402 supplies power to the various components, under control of the electronic controller 404. A Liquid Crystal Display (LCD)/Touch-screen unit 406 may be used to program and operate the controller 404, and/or to monitor feedback from the Patient Interface Device 16, as will be described in greater detail below. A beeper (or other audible and/or visible warning indicia) 405 preferably provides feedback to caregiver(s) when input and/or feedback may be required. The electronic controller 404 controls one or more of preferred brushless DC motor(s) 408 via wiring 481. The DC motor(s) 408 preferably drive(s) a scroll compressor 410 to provide non-pulsate air to a gas inlet 411 of a pressure vessel 412. Ambient air is provided to the scroll compressor 410 via an air filter 414 and an air intake line 416.

The pressure vessel 412 preferably comprises a pressure tank together with appropriate connectors. Preferably, the pressure vessel 412 has an overpressure safety valve 418 to permit escape of air from an over-pressured pressure vessel 412. Preferably, the safety valve 418 also includes a pressure sensor 419, which sends an overpressure signal via wiring 420 to the controller 404. The controller 404 may then command the DC motor 408 to cease pressuring the pressure vessel 412. The pressure vessel 412 also preferably has a working pressure sensor 422 which senses pressure within the pressure vessel 412 and provides a pressure signal to the controller via the wiring 424. A water trap 426 is preferably coupled to the pressure vessel 412, and provides fluid to the Patient Interface Device 16 through a fluid line 428, a fluid connection 428, and a patient interface connector 470, to be described in greater detail below. Electrical wiring 432 preferably connects the electrical controller 404 to the patient interface Device via electrical connections 434 and patient interface connector 470. Of course, the connection between the Driver Unit 10 and the Patient Interface Device 16 may be wired, wireless, or a combination of both.

In use, the Driver Unit 10 preferably provides at least one source of non-pulsatile compressed gas and employs the programmable electronic controller 404 and the touch screen display 406 in order to configure the percussive session. For example, the controller 404 and touch screen display 406 may be used by a caregiver to set one or more session percussive frequencies e.g., 100-200 or 100-400 cycles/min, and working pressures e.g., 20-30 or 20-40 psi, supplied to the Patient Interface Device 16. The controller 404 may also monitor the delivered therapy (from the Patient Interface Device 16) to provide feedback to the caregiver, e.g. treatment duration, e.g., 15-30 minutes, or 15-60 minutes, patient proximal pressure e.g., 5-10 or 5-20 cm H2O, etc. The controller 404 may also provide information to service personnel e.g. hours use, fault conditions etc. The touch screen display 406 provides easy and quick access to system parameters, monitoring data and any fault conditions, and also integrated a built-in protocol to walk the caregiver through setting the system up for optimum therapy.

In use, the Driver Unit 10 preferably provides a source of non-pulsatile compressed air to the Patient Interface Device 16. The air pressure of e.g., 10 psi to the Patient Interface Device is preferably adjusted by the electronic controller 404, which powers the compressor 410. The electronic controller 404 preferably interface with the 4.3" graphic LCD display with integrated touchscreen 406, allowing therapeutic parameters to be configured by the caregiver(s). The electronic controller 404 also preferably processes signals from sensors embedded within the Patient Interface Device (to be described below) and show those feedback signals on the display 406. The electronic controller 404 preferably also monitors overall system health, and usage by the caregiving and/or service staff, and also preferably stores recorded session information for physicians to monitor therapeutic progress. For example, Pressures, Frequency, time, Inspiration/Expiration ratio, spirometry, alarms, etc., may be set, adjusted, controlled, stored, etc., with the controller 404.

In preferred use, the Driver Unit 10 employs a small, low-voltage, typical 24V@¼ HP, brushless motor 408 to drive an oil-less scroll compressor 410, powered by the electronic controller 404. A replaceable filter 414 preferably cleans ambient air for supply to the air compressor 410. The compressor 410 preferably fluidly feeds a small, lightweight pressure vessel 412 (which may be composite construction or lightweight alloy adapted for low working pressures, such as 20 psi), which then supplies the Patient Interface Device 16 via a one way valve 429, the water trap 426, and the connecting hose 428. The pressure within the pressure vessel 412 is preferably monitored by a semiconductor pressure sensor 422, which supplies a pressure reference signal to the electronic controller 404. The electronic controller 404 continuously varies the energy to the DC compressor 410 to provide sufficient air pressure and flow to the Patient Interface Device 16, while reducing energy consumption to a minimum, and hence reducing noise. The pressure vessel (reservoir) 412 also preferably includes the over-pressure relief valve 418 for safety, preferably with an appropriate electrical contact feedback system 419 to the controller 404, which preferably indicates any fault condition to the user.

In use, the electronic controller 404 preferably includes a memory 405 in which a library of protocol settings is maintained. This will allow easier set-up by the caregiver. For example, a preprogrammed setting protocol for a neuromuscular patient is predefined within the controller 404, for example, providing 2 min nebulization, followed by 10 min percussion at 8 Hz, then 5 min at 1 Hz, and complete the treatment with 1 min of nebulization.

Also in use, the Driver Unit 10 preferably includes various alarm and warning features provided by and stored in the Electronic Controller 404. A proximal patient High Pressure alarm is preferably preset at 60 cm H2O, although other and/or additional levels may be provided. If a proximal pressure is detected at the patient proximal pressure sensor (to be described below) that exceeds one or more preset pressure limit, the Electronic Controller 404 is preferably programmed to operate an alarm, e.g., at beeper 405: the alarm will sound and then percussive therapy will cease with an error message displayed on the graphic LCD display 406. A proximal patient Low pressure warning may also be preset at, for example, 5 cm H2O, although other and/or additional levels may be used. If a pressure is detected at the patient pressure sensor that is lower than the preset pressure, the controller 404 is preferably programmed to operate the audible warning 405 and display a message. Preferably, the display 406 will instruct the caregiver to check for leaks within the Venturi Flow Valve and Patient Interface breathing circuit (to be described below), and restart the session. An Exhalation Feedback signal may be configured by the caregiver at the time of initial system setup. Preferably, after the determination of the optimal working pressure, e.g., 20 psi (based on patient chest wiggle (this reflects how effective is the transmission of the percussion/energy wave inside the thorax) and patient comfort (this reflects how easily the patient is able to breath, inhale, and exhale without effort during treatment)), in addition to the patient proximal pressure (e.g., 15 cm H2O), the caregiver will typically set the Exhalation Feedback signal at, for example, 10 cm H2O above the measured proximal pressure amplitude. The exhalation Feedback signal, which preferably comprises an audible beep through beeper 405, assists in training the patient to breathe comfortably through the Venturi Flow Valve within the Patient Interface Device, during the therapy session, teaching the patient to avoid exhaling too hard. Progressive and smooth exhalation permits the lung volume to decrease, making the treatment more effective and reducing the likelihood of overwhelming the patient, especially when very ill. The Exhalation Feedback signal is in fact, educational, teaching the patient how to breathe effectively during the therapy session, which is typically 15 to 30 minutes. Setting the Exhalation Feedback signal is performed by navigating through the Graphical User Interface (GUI) to an Exhalation Alarm Set display screen on the display 406, by using a menu touchscreen control.

To enable therapy to be administered outside of the home environment, the power source for the system preferably comprises a medical grade, high-efficiency switched-mode, mains power supply (to be described below), and this is preferably adapted to be switched out for a replaceable battery pack 402. To reduce weight and improve portability, the battery pack 402 typical comprises lithium-ion cells, or may be, for example, Nickel Metal hydride in cases where transport safety (such as on commercial airlines) is more of a concern. An alternative power arrangement which still facilitates out-of-home use has the Driver unit containing an integral, non-removable, high-efficiency medical grade mains power supply, and also preferably has an automotive auxiliary power cord which obtains 12V power in a car or mobile home.

Figure 5:
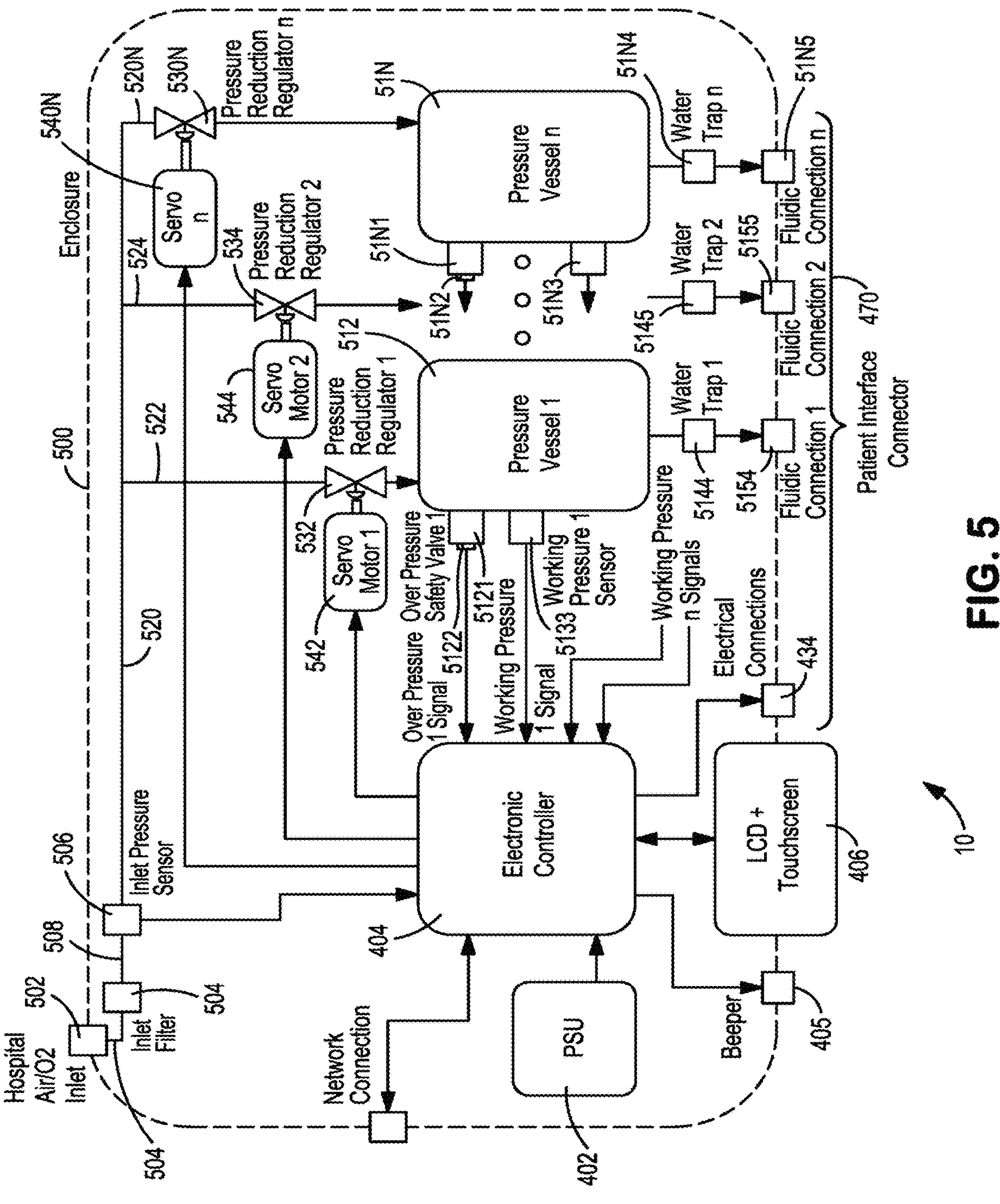
FIG. 5 is a schematic block diagram of an embodiment of the Driver Unit according to the FIG. 3 embodiment.

FIG. 5 is a schematic block diagram of an embodiment of the Driver Unit 10 according to the Hospital embodiment. Pressurized air supply is provided by the hospital through a hospital air/$O_2$ inlet 502 provided in a wall of the enclosure 500. The supplied air/$O_2$ passes via lines/tubing 504 to an inlet filter 506, and to an inlet pressure sensor 506 via lines/tubing 508. Pressurized air is supplied to one or more pressure vessels 512 through 51N, depending on how many pressure levels of air/$O_2$ are to be supplied to one or more patient(s) through the Patient Interface Connector 470. Preferably, the pressurized air is transmitted via lines/tubing 520, 522, 524, and 520N. Such pressurized air is preferably passed through one or more, respective pressure reduction regulators 532, 534, and 530N (as controlled by respective servo motors 542, 534, and 530N) prior to injection into the aforementioned pressure vessels. Preferably, each pressure vessel 512 to 51N has an overpressure valve 5121, 51N1, and sensor 5122, 51N2, as described above. Also, each pressure vessel preferably has a working pressure sensor 5133, 51N3, providing output signals to controller 404, as described above. Likewise, each pressure vessel has a water trap 5144, 5145, 51N4, respectively connected to fluid connectors 5154, 5155, and 51N5, which are installed in the patient interface connector 470, also as described above.

In use, the system may be operated continuously in a standalone mode or in conjunction with an additional third party ventilator for those patients unable to breathe for themselves. The Driver Unit 10 may also be designed to be fail-safe for the patient when operated in standalone mode. Unlike the home care device, in the hospital embodiment, the Driver Unit 10 is preferably provided with a source of high pressure (typically 75 psi) compressed gas (air and/or oxygen) from a hospital outlet, and there may be multiple hoses to the Patient Interface Device 16. The Patient Interface Device 16 preferably provides additional functionality, such as more sensors to monitor treatment, and heating to provide warm air to the patient.

With reference to FIG. 5, in use, the Driver Unit 10 preferably contains an appropriate medical grade power supply 402 suitable for use in cardiac environment. The Driver Unit 10 gas lines preferably contain water traps 5144, 5145, 51N4 preferably adjacent to each pressure vessel outlet, and may also contain heating elements to pre-warm the gas being delivered to the Patient Interface Device 16. The Driver Unit 10 preferably supplies at least one source of non-pulsatile compressed gas to the Patient Interface Device 16. The gas supply may be clean air, oxygen, or blended with an external Oxygen/Air blender, depending on clinical necessity. An alternative embodiment may also include an $O_2$ blender within the Driver Unit 10 for a self-contained system. The Driver Unit 10 preferably contains at least one pressure reduction regulator 532, 534, 530N which may be manually adjustable or, preferably, is motorized and powered by the electronic controller 404. A basic hospital system preferably employs a single pressure reduction regulator 532, and a more sophisticated system employs at least two pressure reduction regulators 532, 53N and associated hoses to supply the Patient Interface Device 16—one regulator to provide a low pressure supply to the Patient Interface Device 16, and another regulator to provide a higher pressure supply for entrainment.

In an embodiment where a fail-safe system is used, each pressure reduction regulator is preferably a "fail-closed" design, redundancy in the form of multiple pressure reduction regulators, and an electronic controller 404 employing multiple processor units, is employed to ensure continued supply in the event that failure of any one regulator or processor would not compromise patient safety. The Driver Unit 10 preferably contains pressure vessels for each pressure reduction valve to act as a surge tank since it known that other devices acting in the vicinity can have an effect on pressure stability, depending on hospital infrastructure. Each pressure vessel preferably an overpressure relief valve for safety and associated fault detection contacts, and also a semiconductor pressure sensor to measure the available pressure.

The electronic controller 404 preferably interfaces with the LCD graphic display and touchscreen 406, allowing therapeutic parameters to be configured and displayed, as well as the working pressures for each line. The electronic controller 404 preferably monitors hospital gas monitor inlet pressure via a pressure sensor 506, and preferably alarms when the inlet pressure is out of tolerance. The electronic controller 404 also processes signals from sensors embedded within the Patient Interface Device 16 (to be described below) and show on the display 406. The electronic controller 404 preferably contains a look-up table and/or control algorithm(s), such as proportional-integral (PI is a type of integrated circuit chip that allows the controller to be able to work as a closed loop, in this case, the controller will be able to adjust the work pressure, according to the change in the proximal pressure delivered to the patient), to adjust the motorized pressure reduction regulators based on feedback from the associated pressure vessel pressure sensor, to provide the desired working pressure. The electronic controller 404 also monitors overall system health, for example, monitoring system and/or component usage for service staff, and storing recorded session information for physicians to monitor patient progress. The electronic controller 404 preferably contains an appropriate interface 434, for example Ethernet, to the hospital network using an appropriate protocol, such as HL7, to permit remote monitoring of patient parameters via a centralized viewing station.

The Connector.

Figure 6:
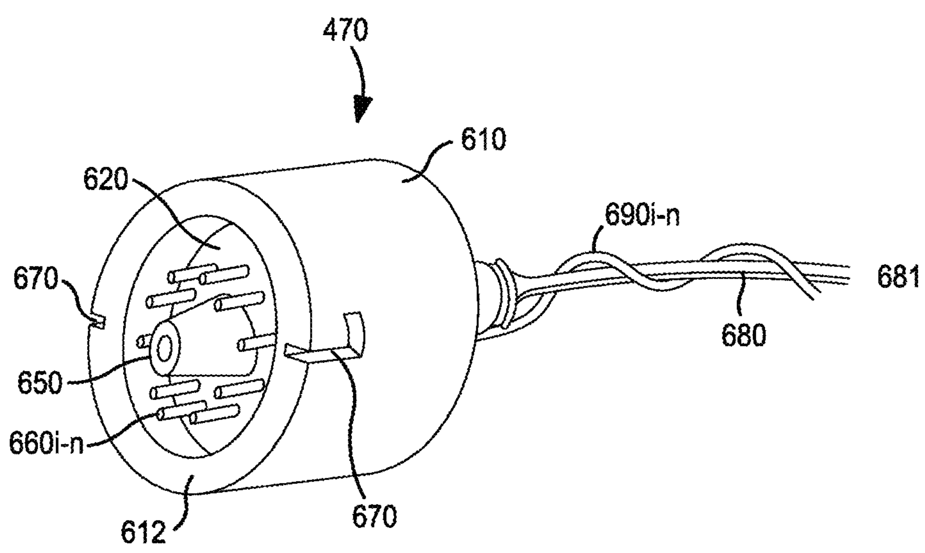
FIG. 6 is a schematic perspective view of a Patient Interface Device Connector for attachment to the Patient Interface Device according to the FIGS. 1-3 embodiments.
Figure 7B:
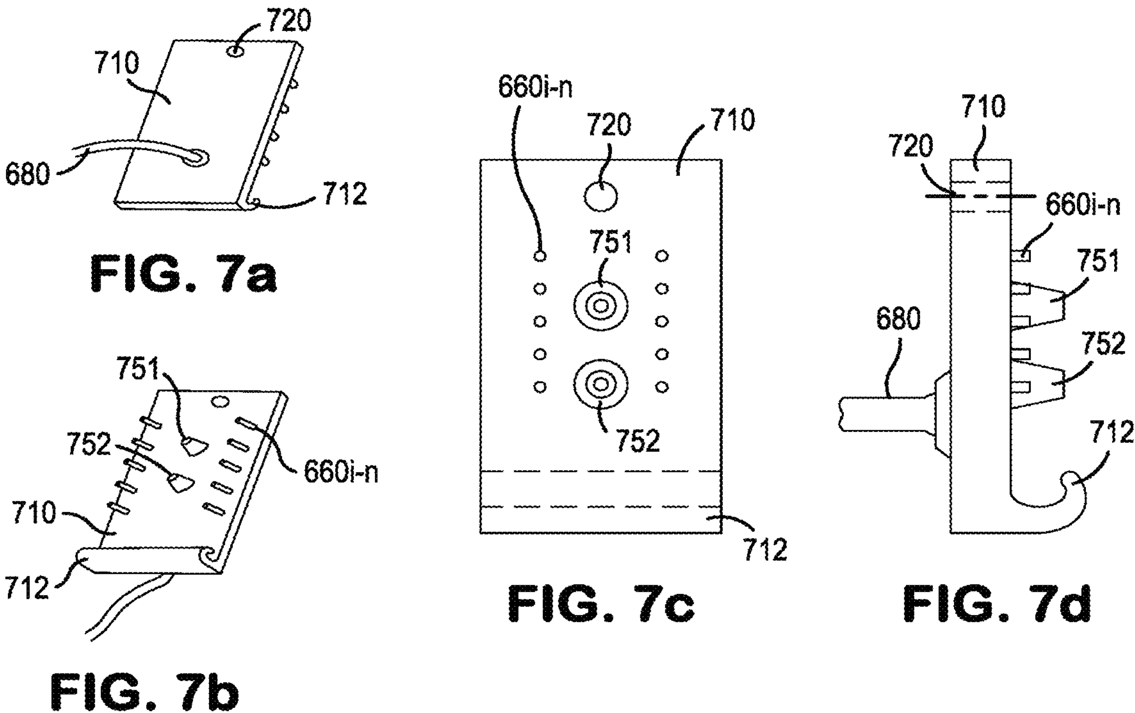

FIG. 6 is a schematic perspective view of a Patient Interface Device connector 470 for attachment to the Patient Interface Device 16 according to the FIGS. 1-3 embodiments. In this embodiment, the quick-disconnect connector 470 preferably has a cylindrically-shaped metal or plastic housing 610 having a recessed inner deck 620 which is round and disposed below a connector lip 612 by a depth that is at least as deep as the height of an air cone 650 and/or the electrical connection pins 660*i* through 660*n*. The air cone 650 supplies the pressurized air to the Patient Interface Device 16, and the pins 660*i* through 660*n* provide electrical communications. The housing 610 preferably includes L-shaped interlocking slots 670 on two or more sides of the housing to lock the connector 470 to complementary locking structure on the Patient Interface Device 16. Pressurized air is supplied through one or more air hose/tube/line 680. Preferably, electrical connection wirings 690*a* through 690*n* are bundles within a sheath wrapped around the air line(s) 680, as shown. In this embodiment, the connector 470 may be affixed to the Driver Unit 10 and detachably coupleable to the Patient Interface Device 16. However, the connector may be affixed to the Patient Interface Device 16 and detachably coupleable to the Driver Unit 10. In another embodiment, there is a connector 470 on each end of an umbilical to detachably couple/decouple the umbilical from both the Driver Unit 10 and the Patient Interface Device 16.

FIGS. 7*a*, 7*b*, 7*c*, and 7*d* are schematic perspective views of a Patient Interface Device Connector 470 according to the FIGS. 1-3 embodiments. In these figures, rectilinear (square and/or rectangular, or a combination of both) solid or hollow housing 710 has an inward-turning lip 712 on at least one edge thereof configured for connection to the patient Interface Device 16. One or more through hole(s) 720 is/are provided to secure the housing 710 to the Patient Interface Device 16 via a securement device, such as a screw, toggle, lever, etc. Air supply cones 751 and 752 are provided for supplying high and lower pressure air and/or $O_2$; of course more or fewer air cones may be supplied. Electrical connectors 660*i* through 660*n* are preferably supplied in two rows complementarily disposed on either side of the air cone(s).

In use, the Driver Unit 10 provides at least one continuous source of compressed air to the Patient Interface Device 16, and also provides electrical connections. To avoid confusion and incorrect connections, the Patient Interface Device air hose and connector assembly preferably employs an integrated connector, where fluidic pressure lines are contained within an umbilical with spirally wound electrical wires. The connector 470 preferably comprises at least one centrally-mounted air-line cone connector(s), with electrical connector pins radially (and/or linearly) spaced around the cone connector(s), contained within the housing and employing a suitable ergonomic locking mechanism appropriate for the target user, such as quarter turn locking collar, lip-and-screw, etc. In the case of multiple air lines, a double lumen fluidic connector may be employed. Alternatively, the Patient Interface Device connector 470 may comprise a rectilinear housing 710 with conical air-line connectors to one side, and electrical pin or flat surface connectors to the other, and preferably employs a removable hinge on one side and a quarter turn locking key mechanism on the other, as shown in FIG. 7*a*. Additionally, one or more insulated heating element(s) 681 may also be present inside the air hose 680 to warm the compressed gas to a temperature more suitable for therapeutic delivery, the temperature preferably being monitored by at least one temperature sensor(s) 811 (FIG. 8) in the Patient Interface Device 16.

The Patient Interface Device.

Figure 8:
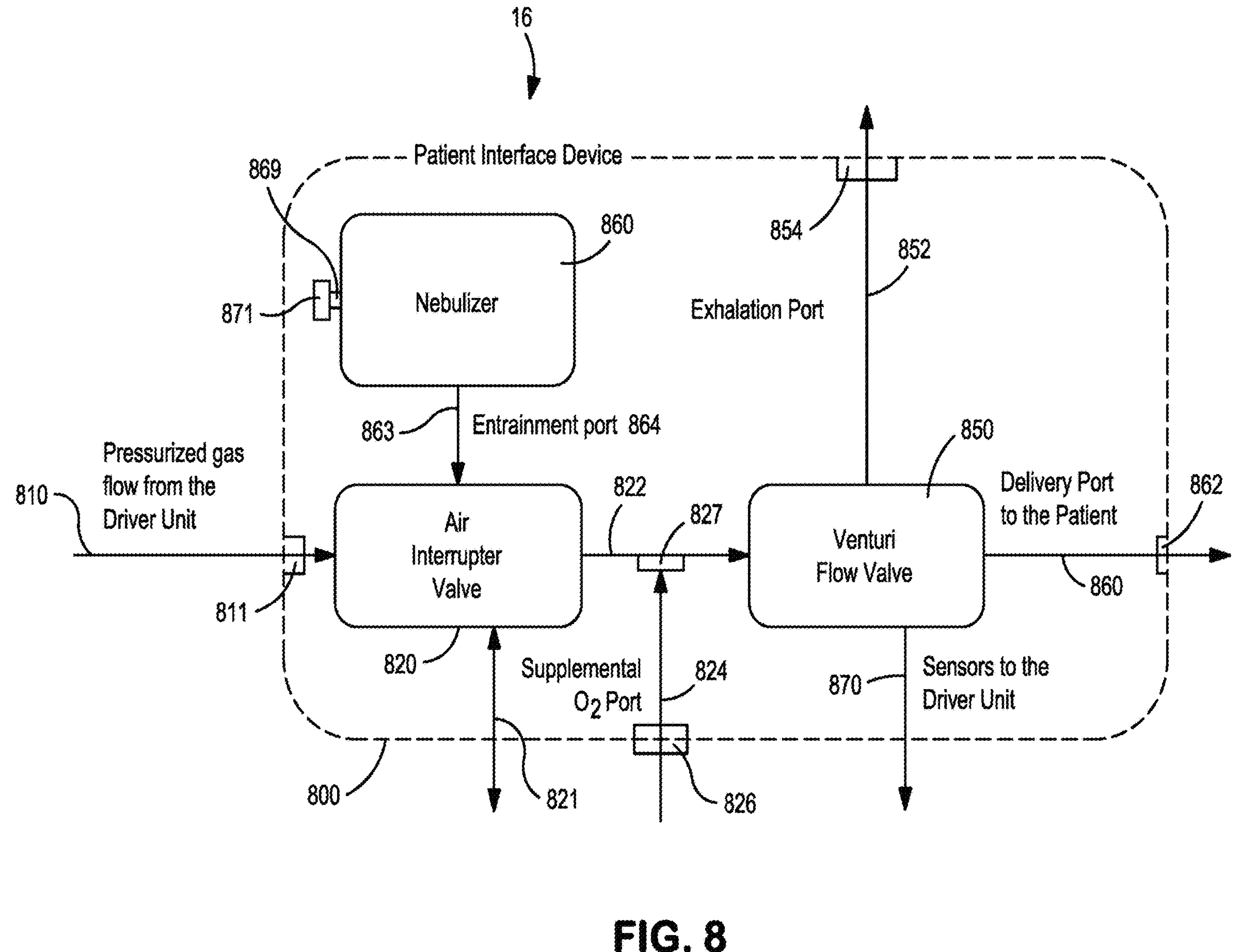
FIG. 8 is a schematic block diagram of an embodiment of the Patient Interface Device according to the FIGS. 1-3 embodiments.

FIG. 8 is a schematic block diagram of an embodiment of the Patient Interface Device 16 according to the FIGS. 1-3 embodiments. The device 16 preferably includes a housing 800, a pressurized gas inlet tube/line/hose 810, a temperature sensor 811, an air interrupter valve 820, a Venturi flow valve 850, and a nebulizer 860. The nebulizer supplies appropriate medications to the air interrupter valve 820 through one or more lines 862 through an entrainment port 864. Pulsed and pressurized gas is supplied from the air interrupter valve 820 through one or more tubes/lines/hoses 822 to the Venturi valve 850. One or more supplemental gas(es) (such as $O_2$) may be supplied to the line 822 through lines/tubes/hoses 824, through a supplemental gas port 826 disposed in a wall of the enclosure 800. The Venturi valve 850 may vent exhalation gas through one or more flexible hoses/tubes/lines 852 through one or more exhalation port(s) 854 in a wall of housing 800. The Venturi valve 850 preferably supplies one or more pulsed and pressurized gasses to the patient through one or more hoses/tubes/lines 860 through one or more delivery port(s) 862 disposed in a wall of the housing 800. Preferably sensors within the Venturi valve 850 (to be described below) supply signals to the electronic controller 404 through electrical wiring 870.

In greater detail, The Patient Interface Device 16 preferably comprises the Venturi flow valve 850, which functions as a flow-to-pressure and pressure-to-flow converter, and an air interrupter valve in order to create pulsatile burst(s) of air/gas to generate the percussive effect. The nebulizer 860 preferably administers medications and/or humidifies the breathing gas to the patient. Preferably, the Venturi 850 is designed to provide a pressure-flow and flow-pressure conversion, where the first pulses of gas preferably generate maximal entrainment from the air entrainment port 864, and the delivered sub-tidal volumes of gas to the patient airway are large. Subsequently, the progressive increase in pressure in the patient airway will be reflected in the delivery port 862 of the Venturi flow valve 850 and, according to the Venturi theory, the pressure inside the valve body will increase, becoming ambient, and decreasing the entrainment flow. Consequently, sub tidal volumes delivered to the patient airway become smaller and smaller and eventually reach equilibrium. This is termed sub tidal ventilation exchange; at this stage each sub tidal volume delivered will be followed by one sub tidal volume of gas exhaled from the patient airway and released across the valve exhalation port 854, full gas exchange will occur, and the patient will be oxygenated and ventilated during the entire therapy session. Exhaled gas from the patient will leave the valve through the exhalation port 854, which may also contain an adjustable resistance-to-flow to facilitate stabilization of the upper airways, especially in patients with pulmonary exacerbation.

The Patient Interface Device 16 preferably contains the air-interrupter valve 820, which may assume a variety of forms appropriate for introducing and/or creating high frequency pressure pulses when acting upon pressurized gas flow from the Driver Unit 10. The air-interrupter valve 820 is preferably configured to repeatedly open and close an internal orifice in response to signals from the controller 404 through electrical wiring 821 to create a pulsatile pressure flow over a large range of frequencies and pressures, such as 1-15 Hz. In addition, a supplemental port 826 may also be provided for those patients receiving supplemental oxygen, which is also entrained in a port 827 in a similar manner as the air entrainment port 864. These ports can be capped when not in use.

Figure 9A:
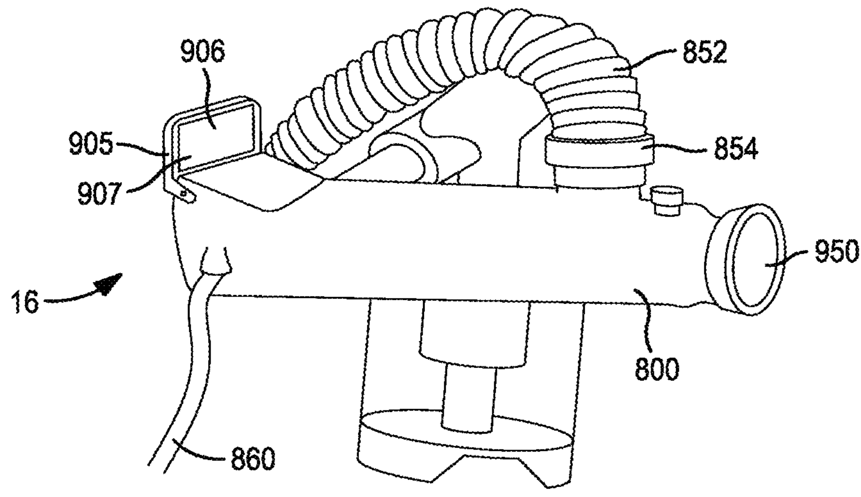
FIG. 9*a* is a schematic perspective view of an embodiment of the Patient Interface Device according to the present invention.
Figure 9B:
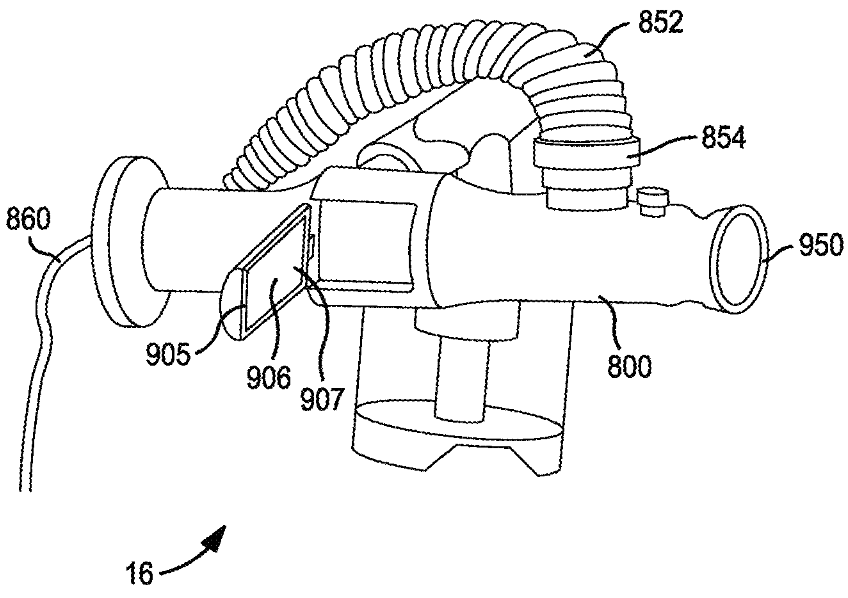
FIG. 9*b* is a schematic perspective view of another embodiment of the Patient Interface Unit according to the present invention.

Referring to FIGS. 9*a* and 9*b*, a Patient Interface Device 16 intended for short-term for home use is shown. Preferably, this Patient Interface Device 16 employs fully short-term reusable parts, as this reduces per use costs and it is acceptable for certain elements of the device to be cleaned, for example, by hand and/or in a dishwasher. Such reusable parts may include one or more of the air interrupter valve 820, the Venturi valve 850, the nebulizer 860, and/or the various lines and ports. Such are typically single-patient-use disposable structures, which the patient reuses for the duration of a short term stay (typically a few days) and then discarded.

The Patient Interface Device 16 may also contain a secondary electronic controller 905 and small LCD display 906, in addition to user interface controls 907, to provide localized visual feedback and also permit minor adjustments of the therapy session. The display and controls may be provided on a hinged, flip-up/down structure similar to current video camera devices.

The air interrupter valve 820 is preferably an electro-mechanical system mounted in the Patient Interface Device 16. The preferred embodiment does not employ needle valves in providing the pulsatile flow to the patient—any valve responsible for delivering pulsatile flow to the patient preferably opens and closes abruptly, to maximum pressure waves in order to maximize the percussive effect. This can be achieved by employing one or more solenoid operated poppet valve(s) (to be described below) and a buckling compression spring (also to be described below) to preferably provide non-linear spring pressure, or by pre-loading the poppet valve with bias pressure from a fine drilling in the structure to allow the valve to open and close instantaneously, the fine drilling will allow gas to escape, decompresses the space around the poppet and consequently reduces the resistance of air when the poppet will move back and forth. The electronic valve percussive frequency (e.g., 100-900 cycles per minute) and duty cycle (e.g., 0-50 cycles per minute) are preferably adjusted via electrical signals from the Driver Unit electronic controller 404.

In use, the air interrupter valve 820 preferably feeds a jet assembly which directs pulses of air into the Venturi valve 850. This creates a sub-atmospheric pressure area around the jet assembly, ahead of the Venturi system, which is open to a secondary chamber via an air entrainment port. The nebulizer 860 is preferably coupled to the Venturi valve via the entrainment port 864, and the nebulizer 860 preferentially supplies the Venturi valve 850 via the entrainment port 864 due to the sub-atmospheric pressure ahead of the Venturi, further developing a pressure gradient across the nebulizer. The nebulizer 860 may also comprise a secondary air inlet 869. The secondary inlet 869 is preferably capped with a one way flapper valve 871 to limit the escape of medicated aerosol, and to reduce unwanted exposure to care givers, in addition to providing a supplemental therapeutic air inlet which may be entrained by the Venturi valve 850.

An embodiment of the nebulizer 860 may comprise an aerosol generator which accelerates a stream of medicated liquid, delivered via capillary action from a bowl, which exits a jet nozzle at high speed. The jet stream then impacts a spray bar, generating an aerosol. The aerosol is drawn into the Venturi valve 850 via the entrainment port 864. The nebulizer 860 may be disposable. A preferred embodiment employs a piezoelectric ultrasonic nebulizer 860, as these do not require compressed air, further reducing the compressed air consumption and hence lowering driver unit power consumption and noise. The ultrasonic nebulizer 860 is intended to be reused and is designed to be fully sterilizable. Within the ultrasonic nebulizer 860 is an ultrasonic generator, which comprises a domed aperture plate with precission-formed holes that control the size of the aerosol droplets and a piezo-vibrational element that creates micro-pumping action to aerosolize medication. Gravity brings the medication in contact with the aerosol generator; the liquid is then drawn through the aperture plate and converted into an aerosol. Upon receiving the corresponding selection by the caregiver at the display control GUI 907, the controller operates the nebulizer.

The Venturi flow valve 850 preferably functions as a flow-to-pressure and pressure-to-flow converter. The Venturi valve 850 preferably comprises the Venturi, the 864 entrainment port, the patient connection orifice 950, the exhalation port 854, and a jet nozzle assembly. Based on the Venturi principle, the Venturi valve 850 delivers variable sub-tidal volumes depending on the patient's airway characteristics, acting as an inhalation/exhalation valve all in one, and generating a substantially single level of positive airway pressure.

FIG. 10*a* through 12*b* show embodiments of a static Venturi valve 850 integral with the disposable part 1002 of the Patient Interface Device 16, with the reusable part 1004 comprising electro-mechanical and/or pneumatic operated interrupter valves.

Figure 10A:
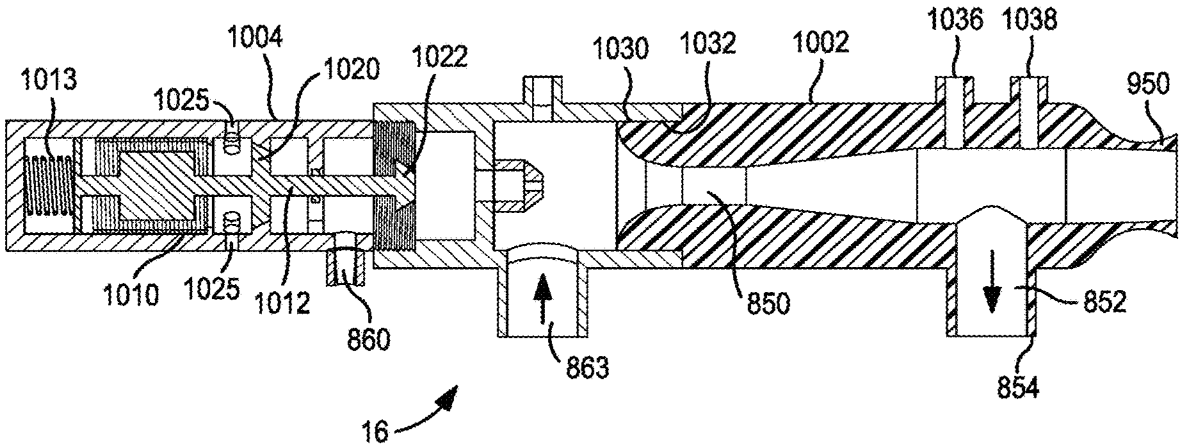
FIG. 10*a* is a schematic cross-section view of an embodiment of the Patient Interface Device according to the present invention.
Figure 10B:
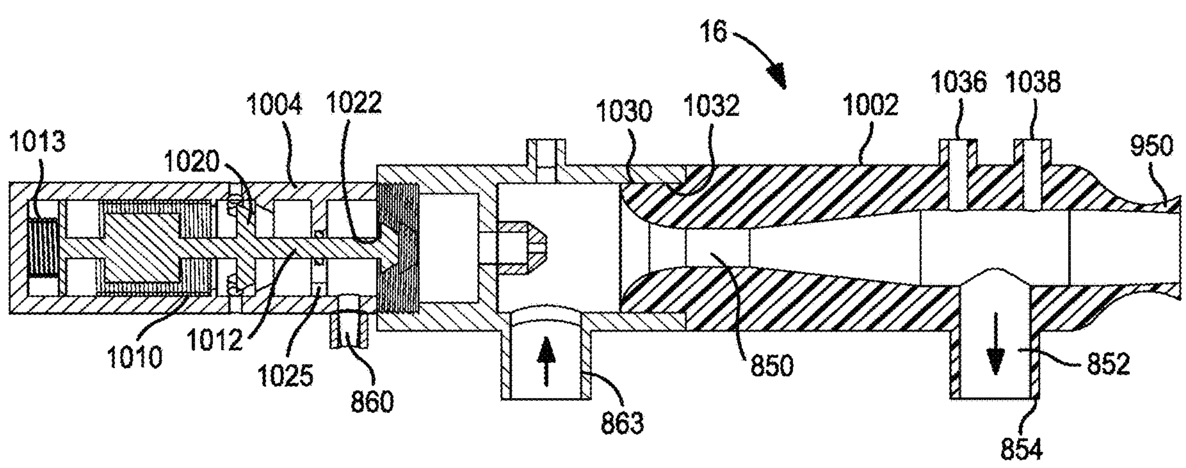
FIG. 10*b* is a schematic cross-section view of another embodiment of the Patient Interface Unit according to the present invention.

FIGS. 10*a* and 10*b* show the electro-magnetic air interrupter system which comprises the disposable part 1002 and the reusable part 1004, where the reusable part 1004 preferably comprises a solenoid 1010, where a solenoid armature shaft 1012 forms two poppet valve systems 1020, 1022. The disposable part 1002 preferably comprises a fixed Venturi flow valve 850, and the reusable part 1004 is preferably screwed onto the disposable part 1002 via threads 1030, 1032, before use. Preferably, one poppet valve 1022 supplies gas to the Venturi valve 850, and a second poppet valve 1020 is biased by one or more drilling tube(s) 1025 (FIG. 10*a*) from the gas feed 860. When the system is open, gas goes from 860 to 1025 then through the poppet 1020 and escapes via the two lateral narrow drilling tubes. FIG. 10*a* shows closed poppet valves, and FIG. 10*b* shows open poppet valves. The right hand end of the shaft 1012 functions as a poppet valve 1022 for the Venturi valve jet system 850, and a secondary, larger poppet valve 1020 also acts as a pressure servo, biasing the valve assembly on the verge of opening via a narrow drilling tube from the chamber adjacent the primary poppet valve 1022. Once the solenoid 1010 is energized, the force on the secondary valve head in conjunction with the biased secondary poppet valve 1020 quickly opens both poppet valves 1020, 1022, permitting air to be delivered via the jet assembly 860 to the Venturi valve 850. The biasing gas pressure on the secondary poppet valve 1020 is vented after it opens. Once the solenoid 1010 is de-energized, a return spring 1013 closes both valves 1020, 1022, and the cycle repeats. Alternatively, a voice coil system may be used to provide bi-directional control of the valve shaft 1012 by replacing the solenoid armature with a permanent magnet. In addition, a secondary solenoid may be employed to synchronously occlude the expired air-port 854, either fully or partially, to maximize the proximal patient Positive Expiratory Pressure (PEP) effect. One or more ports 1036, 1038 provide access to measure such parameters as flow, pressure, spirometry, etc.

Figure 11A:
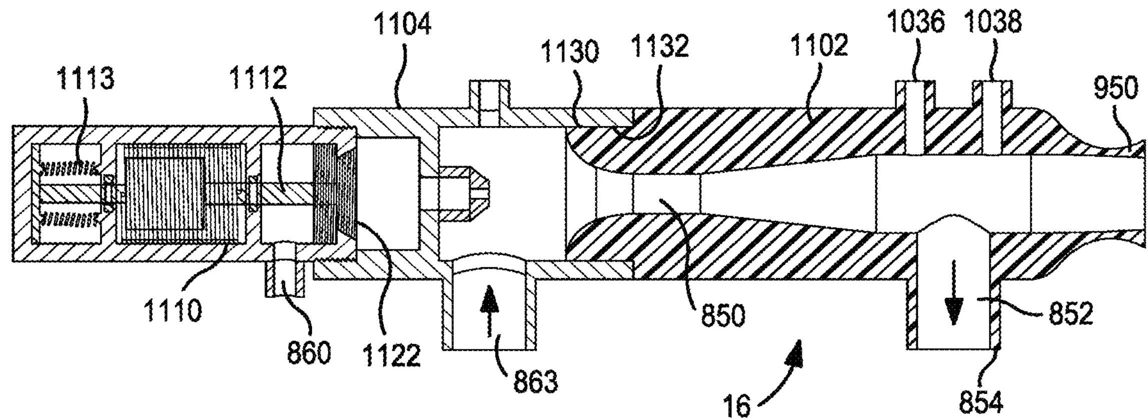
FIG. 11*a* is a schematic cross-section view of an embodiment of the Patient Interface Device according to the present invention.
Figure 11B:
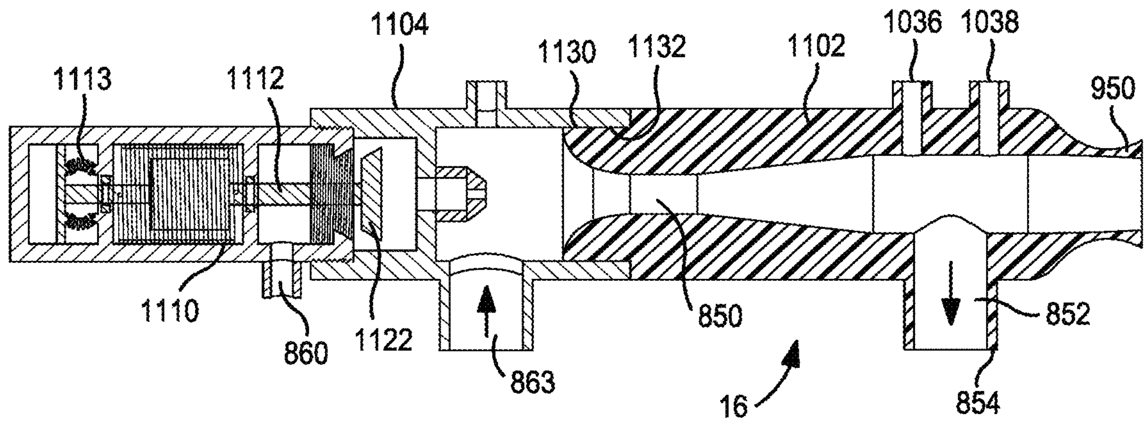
FIG. 11*b* is a schematic cross-section view of another embodiment of the Patient Interface Unit according to the present invention.

FIGS. 11*a* and 11*b* show an electro-magnetic air interrupter system which comprises a disposable part 1102 and a reusable part 1104, where the reusable part 1104 comprises a solenoid valve 1110, and a buckling compression spring 1113 to provide a non-linear spring force. The disposable part 1102 preferably comprises a fixed Venturi valve 850, and the reusable part 1104 preferably is screwed onto the disposable part, via threads 1130, 1132 before use.

Preferably, the reusable part 1104 employs the solenoid 1110 to activate a poppet valve 1122, wherein the poppet valve is biased on the verge of opening using the non-linear spring 1113. FIG. 11*a* shows a closed poppet valve 1122, and FIG. 11*b* shows an open poppet valve 1122—note the buckled spring 1113 in the open position. The right hand end of the solenoid armature shaft 1112 functions as a poppet valve 1122 for the Venturi valve jet system 850, and the gas pressure on the poppet biases the buckling compression spring 1113 so the poppet valve 1122 is on the verge of opening. Once the solenoid 1110 is energized, the valve 1122 opens, and then closes due to the spring 1113 when the solenoid 1110 is de-energized. As in FIGS. 10*a* and 10*b* above, an alternative is to replace the solenoid armature with a permanent magnet to permit bi-directional control of the valve shaft 1112. In addition, a secondary solenoid may be employed to synchronously occlude the expired air-port 854, either fully or partially, to maximize the proximal patient PEP effect.

Figure 12A:
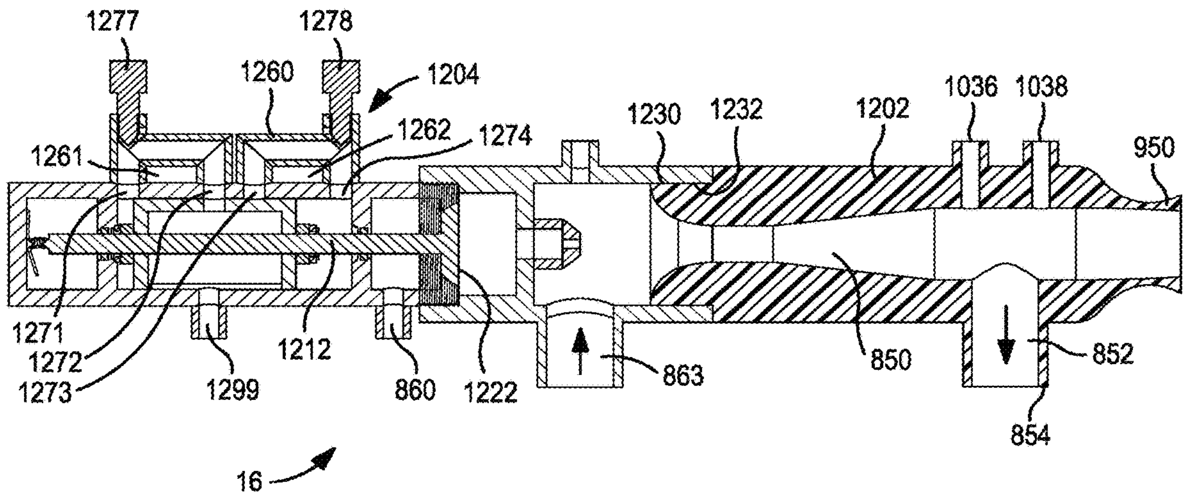
FIG. 12*a* is a schematic cross-section view of an embodiment of the Patient Interface Device according to the present invention.
Figure 12B:
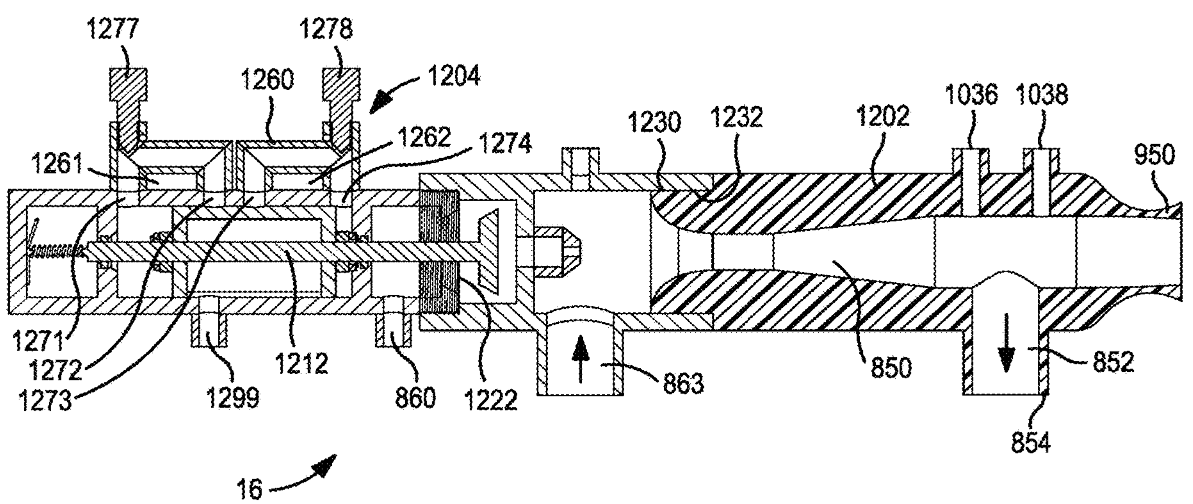
FIG. 12*b* is a schematic cross-section view of another embodiment of the Patient Interface Unit according to the present invention.

FIGS. 12*a* and 12*b* show an electro-magnetic air interrupter system which comprises a disposable part 1202 and a reusable part 1204. The reusable part 1204 preferably comprises a pneumatically operated, double acting shuttle valve 1260, and the disposable 1202 part preferably comprises a fixed Venturi valve 850. The reusable part 1204 is preferably screwed onto the disposable part 1202 via screw threads 1230, 1232, before use.

FIG. 12*a* shows a closed poppet valve 1222 and FIG. 12*b* shows an open poppet valve 1222—note the shuttle valve shaft 1212 moving from side to side. As separate gas supply line 1299 is available for the patient supply and to operate the shuttle, if desired. The pneumatic sliding shuttle 1260 preferably contains airways 1261, 1262 to direct gas under pressure into ports 1271, 1272, 1273, 1274 in the housing. The shuttle valve 1260 typically comprises hardened metal or plastic materials, and is integrated into the reusable part 1204 of the Patient Interface Device 16. Preferably, needle valves 1277, 1278 are used to meter gas venting from each side of the shuttle—once gas pressure in one side of the shuttle exceeds the other, the shuttle moves across. The double acting nature facilitates the active air interrupter closing system 820 in order to sharpen the pressure pulses intended to enhance the percussive therapy efficacy. In a preferred embodiment, the adjustable needle valves 1277, 1278 are preferentially controlled using a motor/servo system where the driver unit electronic controller 404 contains a calibrated table of needle valve settings for desired percussive frequency. A simplified version may omit a needle valve for one or more drillings tube(s), once optimum settings have been determined, such as duty cycle.

Figure 13A:
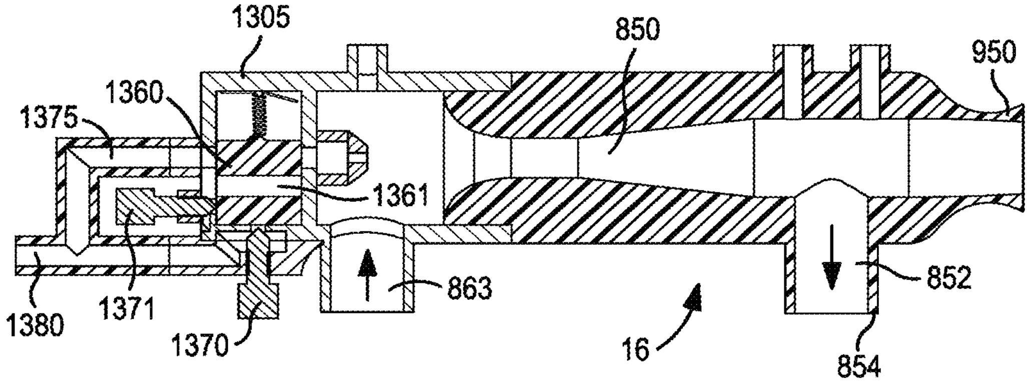
FIG. 13*a* is a schematic cross-section view of an embodiment of the Patient Interface Unit according to the present invention.
Figure 13B:
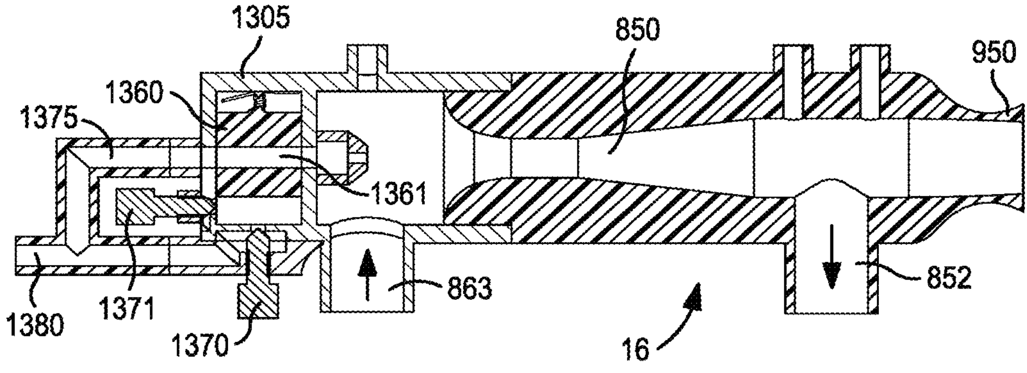
FIG. 13*b* is a schematic cross-section view of another embodiment of the Patient Interface Unit according to the present invention.

FIGS. 13*a* and 13*b* show a Fully Disposable Patient Interface Device 16 comprising an integral, static Venturi valve 850 with an integrated, single-acting, pneumatic air interrupter 1305 employing a sliding shuttle valve 1360. FIG. 13*a* shows the sliding shuttle valve in the closed position, and FIG. 13*b* shows the sliding shuttle valve 1360 in the open position. It is apparent that separate sources of gas 860, 1380, respectively, can be utilized to supply the patient via the Venturi valve 850, and for operating the shuttle valve 1360. The fully disposable patient interface shuttle valve 1360 preferably employs a needle valve 1370 to meter compressed gas into a sliding shuttle valve. The shuttle valve 1360 is preferably held closed by a non-linear buckling spring 1313. When the pressure in the shuttle valve 1360 chamber exceeds a preset threshold, the shuttle overcomes the spring pressing force, and the valve 1360 moves across to open the gas passageway 1375. This opens an airway and via a drilling 1361 in the shuttle 1360, supplies gas to the Venturi valve 850. A second needle valve 1371 vents the chamber formed as the shuttle moved across, and when exhausted, the shuttle 1360 returns home due to the spring force, abruptly closing the gas supply to the Venturi valve 850. This needle 1371 may be replaced by a drilling if a simplified control is desired. Where extra percussion is desired, a sliding Venturi valve 850 may be employed to enhance the percussive effect by generating pressure waves as the Venturi reaches its movement limits.

In use, the adjustable metering needles control the percussive frequency and duty cycle, in conjunction with the Venturi valve 850. The needle valves may be manually operated, and the electronic controller 404 simply counts the operations over time in order to derive percussive frequency. In this case, the Patient Interface Device 16 could be entirely disposable as the sliding shuttle interrupter valve may be constructed of plastic and molded into the Patient Interface Device 16, since this eliminates issues due to surface wear of the shuttle over time. FIGS. 13*a* and 13*b* show a single compressed gas source 1380, but it is apparent an additional gas source, such as $O_2$, could be provided to the patient; and a separate source, such as air, could be employed to control the Venturi valve 850. A preferred embodiment for continuous use comprises the fully disposable Patient Interface Device 16 employing a pneumatic shuttle flow interrupter valve as shown, but configured on the patient interface connection 470 for use with standard ventilation tubes. A fully disposable system is preferred as continuous therapy devices may be used on a single patient and typically disposed of after one week's continuous use, since infection control prevents re-use on different patients. Not requiring sterilization between patients permits the use of low cost medical grade plastics which incompatible with high temperature sterilization. However, a continuous therapy system employing a reusable part and a disposable part is also possible when the reusable part is designed to be sterilized.

The Patient Interface Device 16 of FIGS. 13*a* and 13*b* may be modified, as discussed above, to provide separate gas supplies for the patient (which could be oxygen), and to activate the shuttle (which could be air), hence reducing waste of medical oxygen in hospital settings. A preferred embodiment may also contain heating elements within the Patient Interface Device 16 to warm the gas supplied to the patient. A preferred embodiment may also contain additional sensors in the Patient Interface Device 16 to monitor the administered therapy, for example, $FiO_2$. Provided the heating element(s) are implemented as one or more hot-wire(s), this permits each heating element to also function as a hot-wire anemometer to measure gas speed. The driver unit controller 404 also monitors the electrical power required by the heating element, and is able to calculate the air speed of passing gas as it cools the heating element. The driver unit controller 404 preferably stores and operates an algorithm and/or calibration table, which preferably includes incoming temperature, temperature of gas reaching the patient, and power drawn by the heating elements, to calculate volume gas flow. Employing a second hot wire anemometer in the expiration port 854 permits the volume of gas accepted by the patient to be calculated with an algorithm stored and operated by electronic controller 404 that is thus able to observe inspiration and expiration cycles of the patient, permitting spirometry to be performed.

Figure 14A:
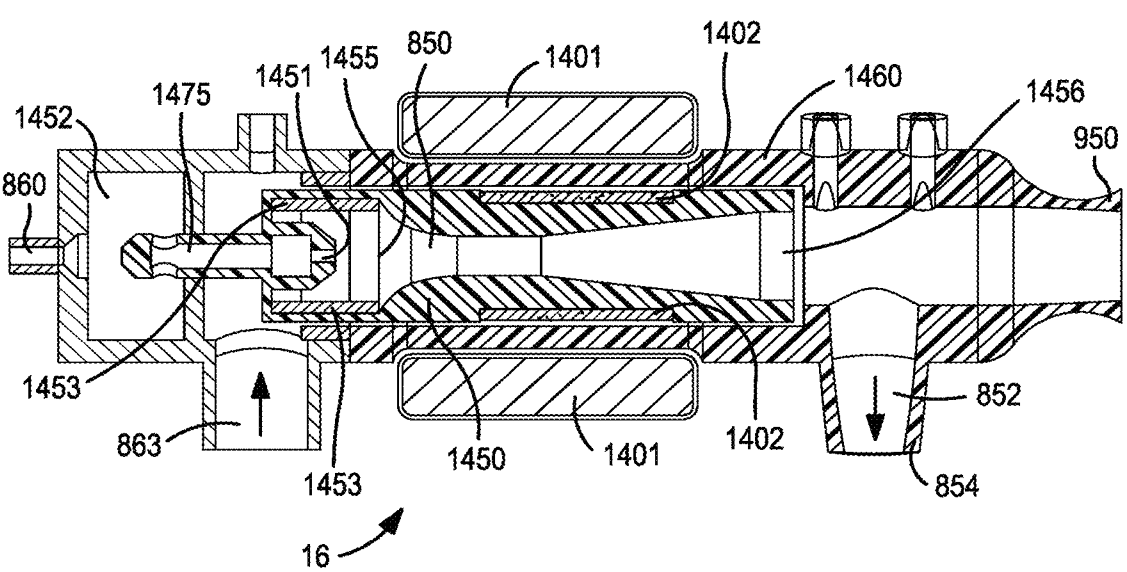
FIG. 14*a* is a schematic cross-section view of an embodiment of the Patient Interface Device according to the present invention.
Figure 14B:
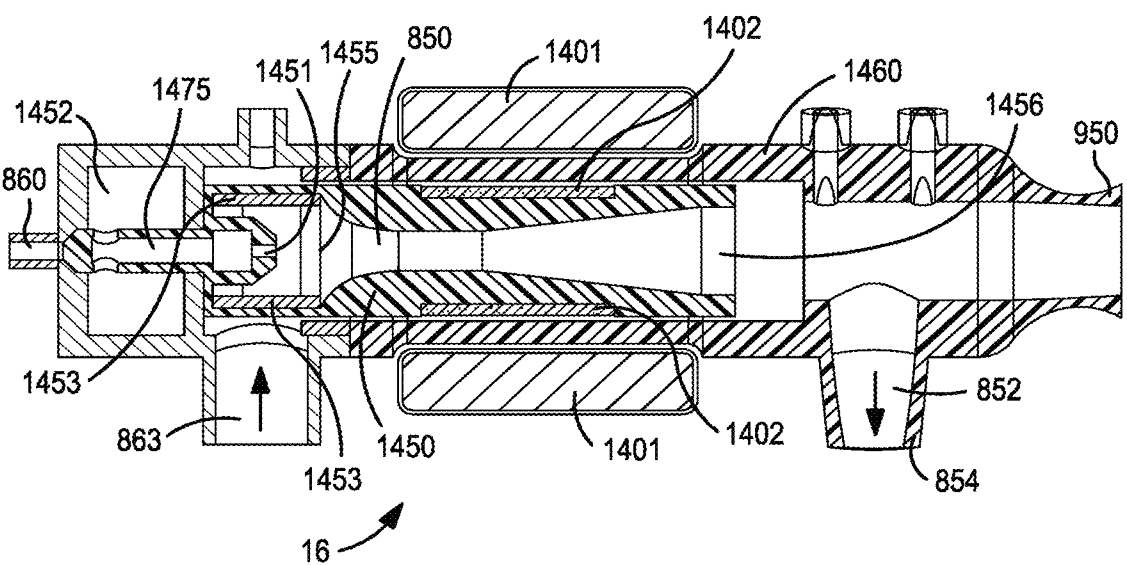
FIG. 14*b* is a schematic cross-section view of another embodiment of the Patient Interface Unit according to the present invention.

FIGS. 14*a* and 14*b* show a fully disposable electromagnetic operated Patient Interface Device 16 comprising a sliding Venturi valve 850 that employs rare earth magnets 1402 molded within a sliding Venturi shuttle body 1450, which slides laterally within a disposable shuttle body 1460, and an external electrical coil 1401 preferably clamped around the disposable shuttle body 1460. The sliding Venturi valve 850 thus acts as an air interrupter valve.

FIG. 14*a* shows the sliding Venturi valve 850 in the right hand position, and the air interrupter 1475 open. FIG. 14*b* shows the sliding Venturi valve 850 in the left hand position, and the air interrupter 1475 closed. Application of a DC electric current of one polarity to the externally mounted electromagnetic coils 1401 forces the movable Venturi valve 850 to slide in one direction, and reversing the polarity forces the movable Venturi valve 850 to slide in the other direction. As the shuttle stroke is typically less than ¼" and the shuttle mass is minimal, the shuttle is easily able to oscillate backwards and forwards at high speed, up to 15 Hz. Monitoring electronics in the electronic controller 404 are able to detect how the current within the coil changes as the shuttle moves, and hence detect whether the shuttle is sliding, or is stuck in pace, and hence in a fault condition.

Preferably, the shuttle 1450 carries the jet 1451 with it, which fluidly communicates with a feed chamber 1452 via a rigid wide bodied communicating tube 1453 to ensure the critical distance between the jet and the Venturi inlet 1455 is maintained regardless of shuttle position, and hence maintain proper entrainment. The wide bodied communicating tube 1453 is occluded with the shuttle in the home, left hand position, also serving as an air interrupter valve. In addition, depending on the location of the outlet port 1456, the disposable shuttle body 1450 may be adapted so that the fully extended shuttle partially or fully occludes the expired air-port 854, increasing average positive airway pressure (PAP).

Figure 15A:
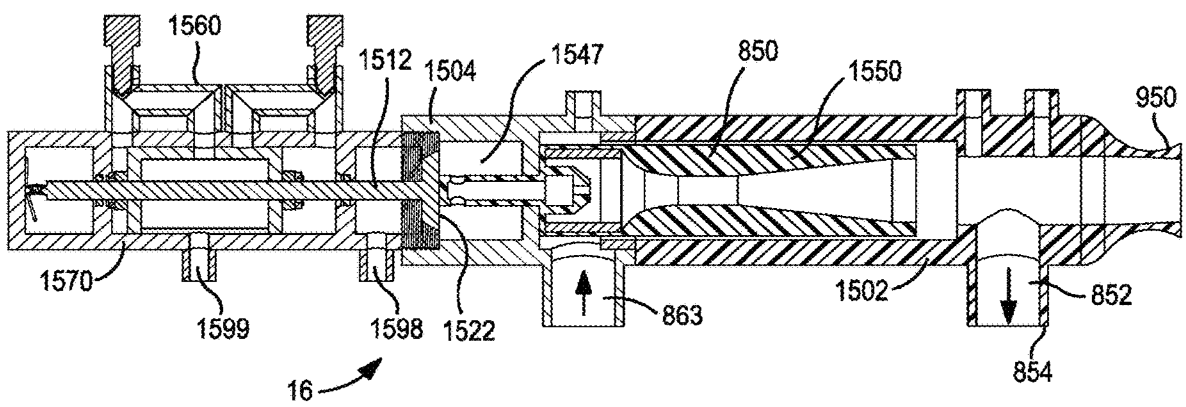
FIG. 15*a* is a schematic cross-section view of an embodiment of the Patient Interface Device according to the present invention.
Figure 15B:
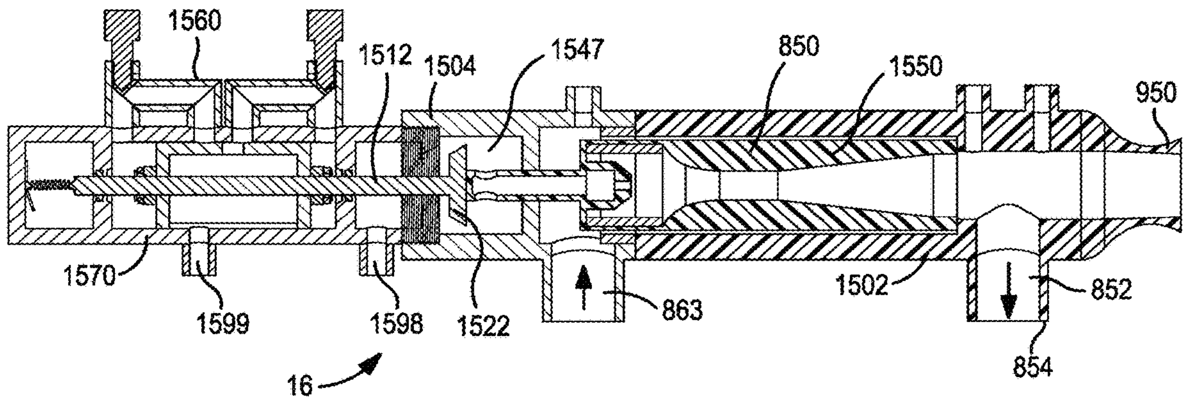
FIG. 15*b* is a schematic cross-section view of another embodiment of the Patient Interface Unit according to the present invention.

FIGS. 15*a* and 15*b* show another Patient Interface Device 16 embodiment, which is an extension of FIGS. 12*a* and 12*b*, in that it comprises a pneumatic bidirectional oscillating air-interrupter valve 1560 with a sliding Venturi shuttle 1550. Patient Interface Device 16 may comprise a disposable part 1502 and reusable part 1504, similar to FIGS. 12*a* and 12*b*. The disposable part 1502 preferably comprises the slidable Venturi valve 850, and the reusable part 1504 preferably employs a pneumatic double acting shuttle valve 1570. FIG. 15*a* shows a closed poppet valve 1522, and FIG. 15*b* shows an open poppet valve 1522—note both the shuttle valve 1570 and Venturi valve 850 are connected (e.g., by welding the poppet valve 1522 with the jet tube) and move from side to side. Separate gas supplies 1598, 1599, respectively, are available for the patient supply and to operate the shuttle, if desired. Here, the oscillating shaft 1512 which supports the pneumatic shuttle valve 850 is extended and fluidly communicates with the sliding Venturi shuttle 1550 from a feed chamber 1547. As the poppet valve 1522 opens in the manner described previously, the sliding shuttle 1550 moves synchronously. The same approach can be taken for the embodiments of FIGS. 10*a*, 10*b* or FIGS. 11*a*, 11*b*, respectively.

Figure 16A:
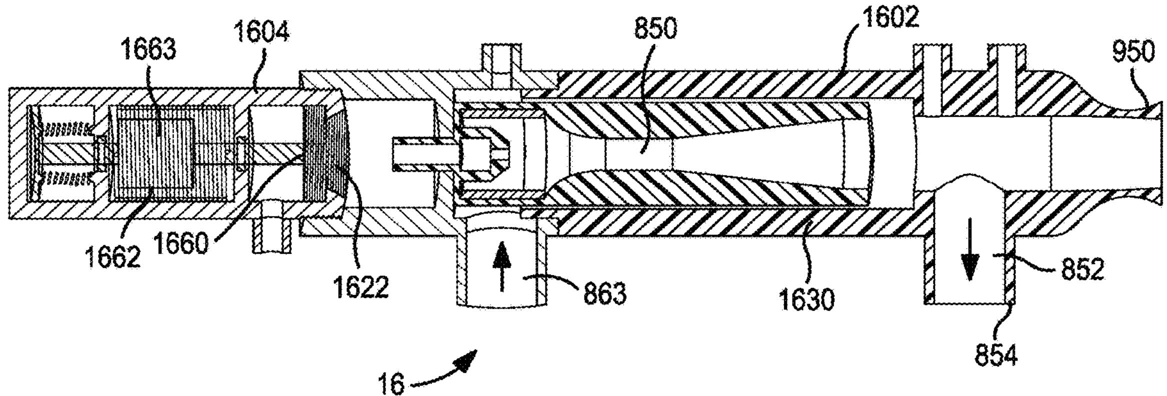
FIG. 16*a* is a schematic cross-section view of an embodiment of the Patient Interface Device according to the present invention.
Figure 16B:
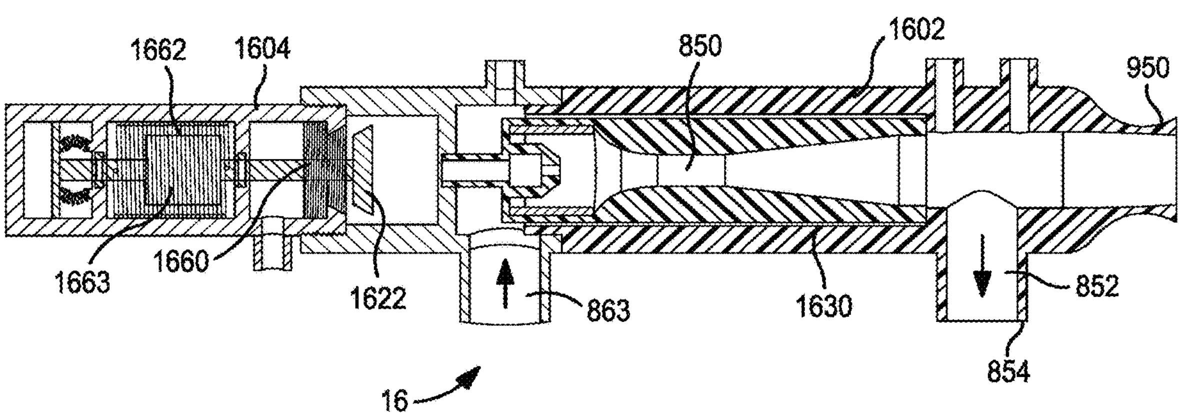
FIG. 16*b* is a schematic cross-section view of another embodiment of the Patient Interface Unit according to the present invention.

FIGS. 16*a* and 16*b* show yet another Patient Interface Device 16 combining the electromagnetic sliding valve principle of FIGS. 14*a* and 14*b*, together with the electromagnetic interrupter of features of FIGS. 10*a*, 10*b* and/or FIGS. 11*a*, 11*b*. Patient Interface Device 16 comprises disposable part 1602 and reusable part 1604 as described above. The disposable part 1602 preferably comprises an electromagnetically activated slidable Venturi valve 850, and the reusable part 1604 preferably employs an electromagnetically activated poppet valve 1622. FIG. 16*a* shows a closed poppet valve 1622, and FIG. 16*b* shows an open poppet valve 1622—note that both shuttle valve 1660 and the slidable Venturi valve 850 may move independently. This embodiment provides maximum flexibility in the administering of percussive pulses and the relative timing of the sliding Venturi valve 850, as shown. The reusable part 1604 preferably comprises the solenoid interrupter valve 1662 and electromagnetic coils 1663. In an alternative similar to FIGS. 14*a* and 14*b*, coils may be clamped around the disposable part 1602, comprising the housing 1630 and the slidable Venturi valve 850. In addition, a secondary solenoid may be employed to synchronously occlude the expired air-port 854, either fully or partially, to maximize the proximal patient PEP effect.

Figure 17A:
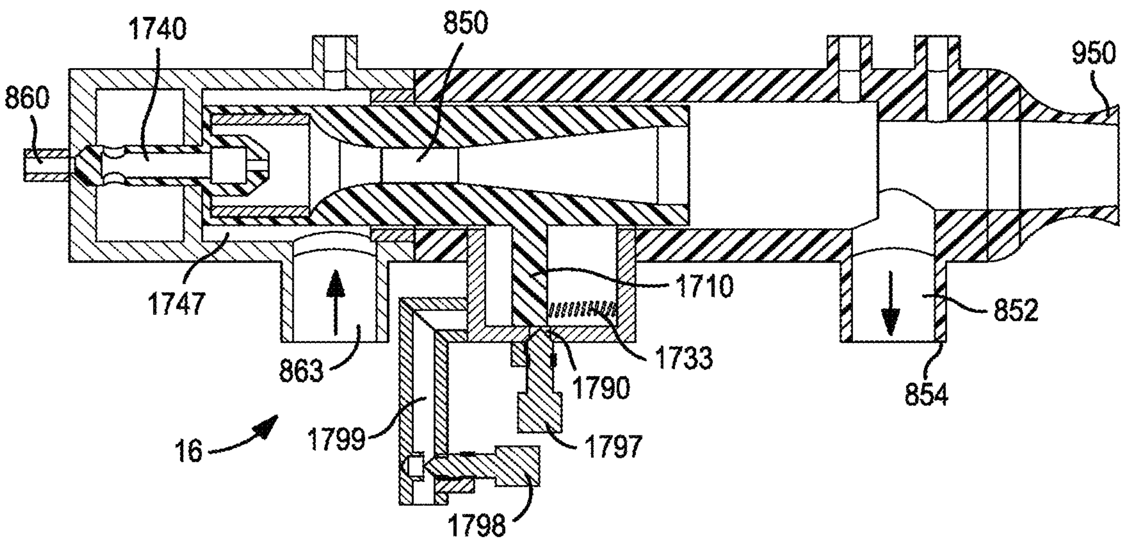
FIG. 17*a* is a schematic cross-section view of an embodiment of the Patient Interface Device according to the present invention.
Figure 17B:
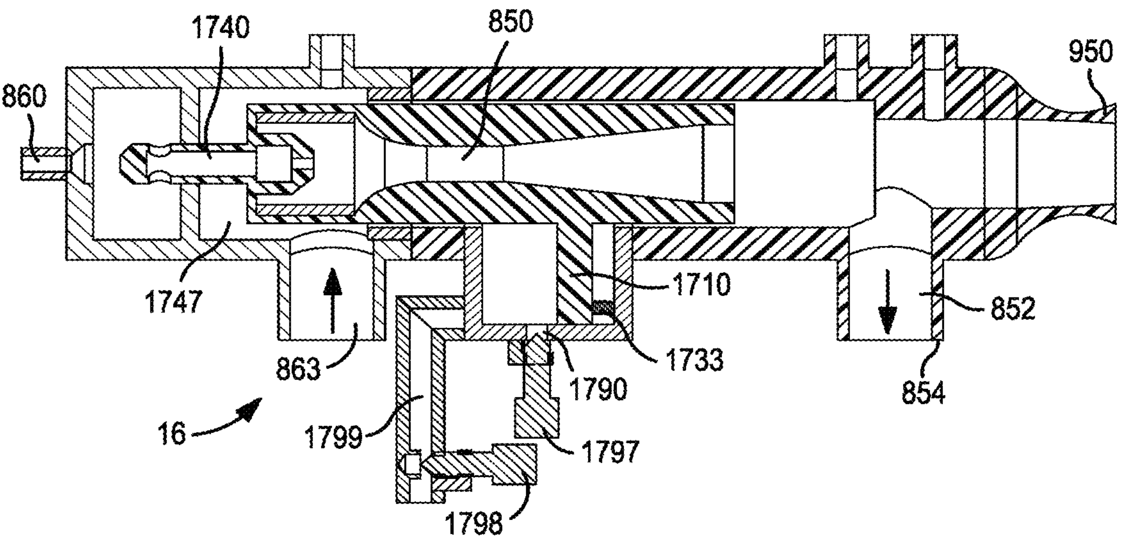
FIG. 17*b* is a schematic cross-section view of another embodiment of the Patient Interface Unit according to the present invention.

Yet another embodiment of a compact, fully disposable Patient Interface Device 16 is shown in FIGS. 17*a* and 17*b*. This embodiment combines a sliding Venturi valve 850 operated by a movable shuttle 1710. Fully Disposable Patient Interface Device 16 preferably comprises a slidable Venturi valve 850 and a movable shuttle valve 1740 as a modification of FIGS. 17*a* and 17*b*. This approach is an extension of FIGS. 13*a* and 13*b*, where the movable shuttle 1710 now activates the sliding Venturi valve 850 synchronously, employing a spring return 1733. The buckling spring 1733 provides non-linear effect wherein a predefined chamber 1747 pressure must be reached before the spring 1733 gives, then permitting the shuttle 1710 to abruptly slide. The vent 1790 is shown with a needle valve 1797 to alter a duty cycle, which would always be adjusted to flow greater than the inlet 1799 needle valve 1798, which controls frequency. A simplified approach may employ a fixed drilling for the vent.

Figure 18A:
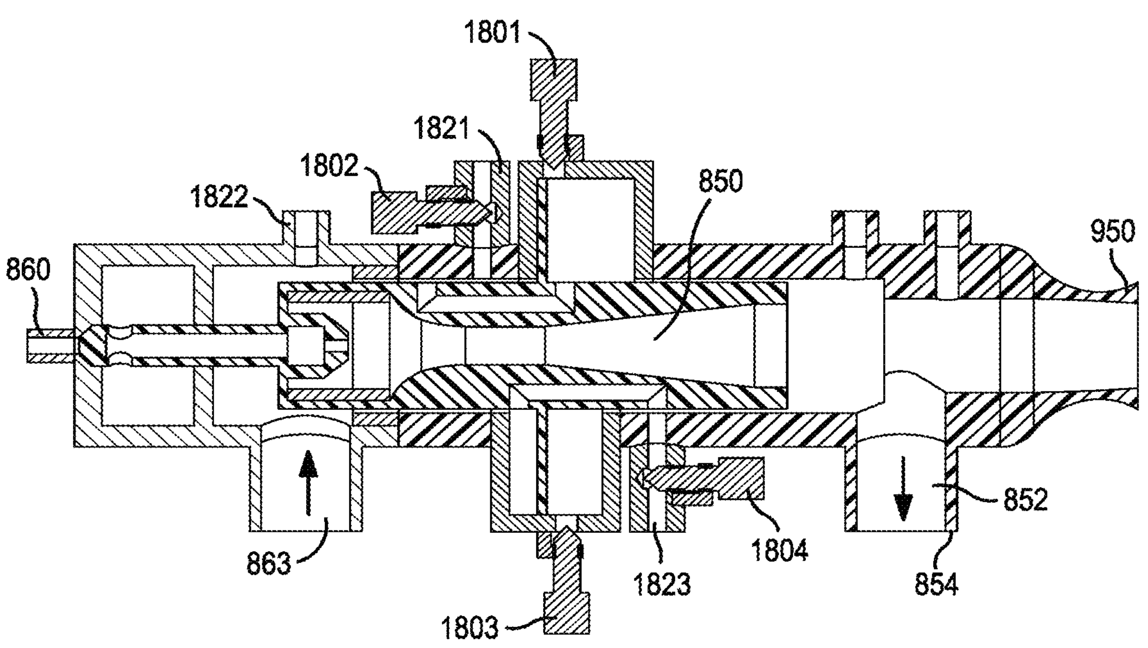
FIG. 18*a* is a schematic cross-section view of an embodiment of the Patient Interface Device according to the present invention.
Figure 18B:
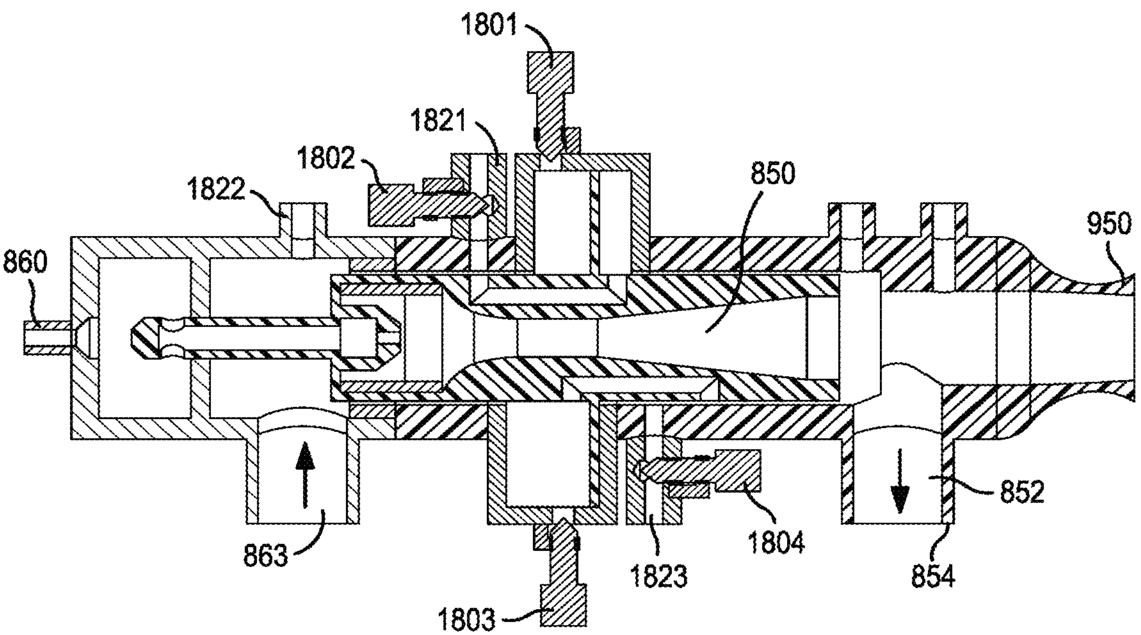
FIG. 18*b* is a schematic cross-section view of another embodiment of the Patient Interface Unit according to the present invention.

FIGS. 18*a* and 18*b* show an additional preferred embodiment which employs a double action to forcibly return the slidable Venturi valve 850, and not rely on spring pressure alone. The double acting pneumatic slidable Venturi valve 850 preferably employs four needle valves 1801, 1802, 1803, 1804 for maximum flexibility in configuration, and up to three gas inlets 1821, 860, 1823. The first gas inlet 860 is for the patient, and may be air, $O_2$, or a combination at an optimum therapeutic pressure. The second gas inlet 1821 is to slide the Venturi valve 850 towards the patient, and employs two needle valves 1801, 1802—one to control the buildup of pressure and to slide the Venturi, and the other one to vent. The third gas inlet 1823, which may be different pressure from the first and second inlets, also has two needle valves 1803, 1804 to control the rate of pressure rise to return the Venturi valve 850 back home, and to vent. The four needle valves and differing pressures permit precise control of frequency and duty cycle. A simpler double acting Venturi valve embodiment may have a single gas supply to both the patient and actuators, and employs a single needle valve to control frequency, with fixed drillings in place of the other needle valves to set the duty cycle, or variations therebetween.

The benefits of distributing part of the system in the Driver Unit 10 and part of the system in the Patient Interface Device 16 include: Relocation of the air interrupter valve to the Patient Interface Device 16 eliminates the damping effects of the column of air within the long connecting hose on the percussive pressure pulses, improving hose wall elastic compliance and increasing efficacy; Reduces the system working pressure required to deliver therapeutic percussive pulses to the patient, lowering system power consumption and noise; and Improved servicing since the Patient Interface Device 16 can be simply be replaced at the Device end of life, without requiring the Driver Unit 10 to be disassembled and retested.

ADSV Embodiments.

ADSV embodiments will now be described. With respect to FIG. 8, the above description pertains, but a sliding Venturi valve 850 is used instead of the previously-described Venturi valve.

Figure 19A:
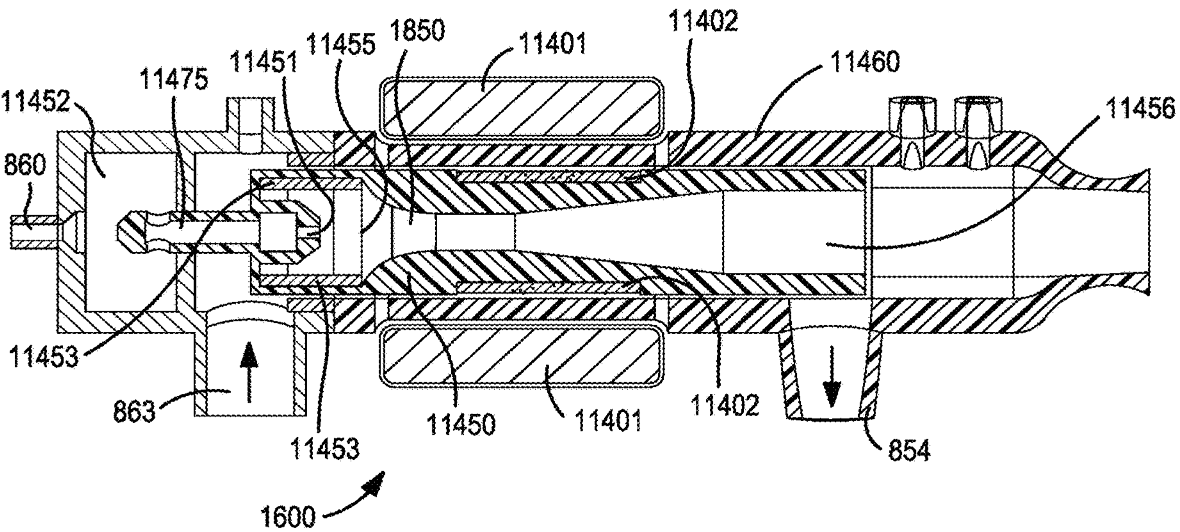
FIG. 19*a* is a schematic cross-section view of another embodiment of the Patient Interface Device according to the present invention.
Figure 19B:
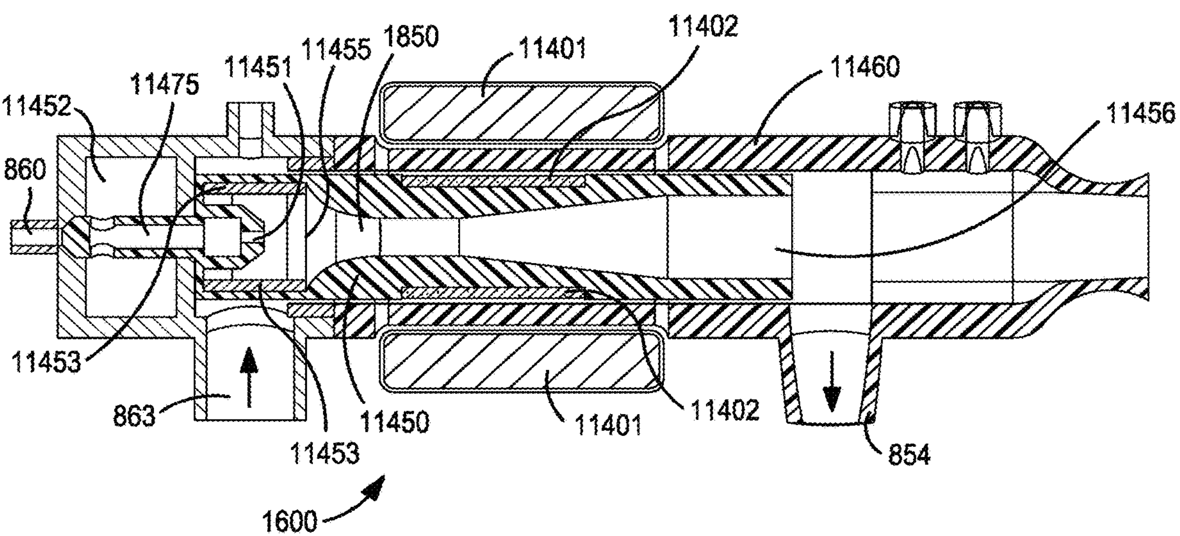
FIG. 19*b* is a schematic cross-section view of the another embodiment of the Patient Interface Unit according to the present invention.

FIGS. 19*a* and 19*b* show a fully disposable electromagnetic-operated Patient Interface Device 1600 comprising a sliding Venturi valve 1850 that employs rare earth magnets 11402 molded within a sliding Venturi shuttle body 11450, which slides laterally within a disposable shuttle body 11460, and an external electrical coil 11401 preferably clamped around the disposable shuttle body 11460. The sliding Venturi valve 1850 thus acts as an air interrupter valve.

FIG. 19*a* shows the sliding Venturi valve 1850 in the right hand position, and the air interrupter 11475 is open. FIG. 19*b* shows the sliding Venturi valve 1850 in the left hand position, and the air interrupter 11475 closed. Application of a DC electric current of one polarity to the externally mounted electromagnetic coils 11401 forces the movable Venturi valve 1850 to slide in one direction, and reversing the polarity forces the movable Venturi valve 1850 to slide in the other direction. As the shuttle stroke is typically less than ¼" and the shuttle mass is minimal, the shuttle is easily able to oscillate backwards and forwards at high speed, up to 15 Hz. Monitoring electronics in the electronic controller 404 are able to detect how the current within the coil changes as the shuttle moves, and hence detect whether the shuttle is sliding, or is stuck in pace, and hence in a fault condition.

Preferably, the shuttle 11450 carries the jet 11451 with it, which fluidly communicates with a feed chamber 1452 via a rigid wide bodied communicating tube 11453 to ensure the critical distance between the jet and the sliding Venturi inlet 11455 is maintained regardless of shuttle position, and hence maintain proper entrainment. The wide bodied communicating tube 11453 is occluded with the shuttle in the home, left hand position, also serving as an air interrupter valve. In addition, depending on the location of the outlet port 11456, the disposable shuttle body 11450 may be adapted so that the fully extended shuttle partially or fully occludes the expired air-port 854, increasing average positive airway pressure (PAP). In fact, the sliding Venturi acts as inspiratory, expiratory valves all in one.

Figure 20A:
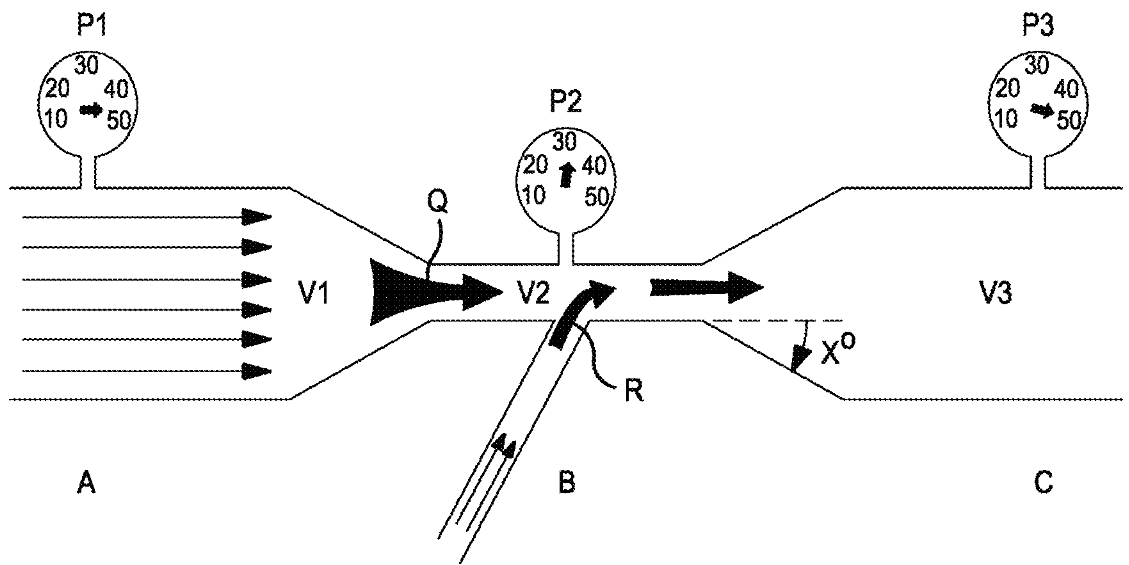
FIG. 20*a* is a schematic view of a Venturi structure entraining a gas.

In operation, when receiving high pressure pulsatile gas flow from the interrupter valve, the Venturi body moves away from the resting position (open position); simultaneously gas passes through the stem passageway into the Venturi entrance and creates a flow acceleration and generates a lower than ambient pressure, due to the Venturi effect. This encourages gas (from ambient, or from a low pressure circuit) to be entrained and enter into the Venturi. Because the Venturi tube has a bigger diameter as his delivery port, the flow will decelerate, recover the pressure, and the subtidal volume is delivered to the patient airways (FIG. 20*a*). The sliding Venturi when driven to its maximal proximal position (occluded position), partially or fully obstructs the exhalation outlet port in order to reduce flow of exhalation gases. When the Venturi slider returns to the initial position (open position) after the applied pulse, the exhalation outlet port fully opens allowing gases to escape (patient exhalation).

Figure 20B:
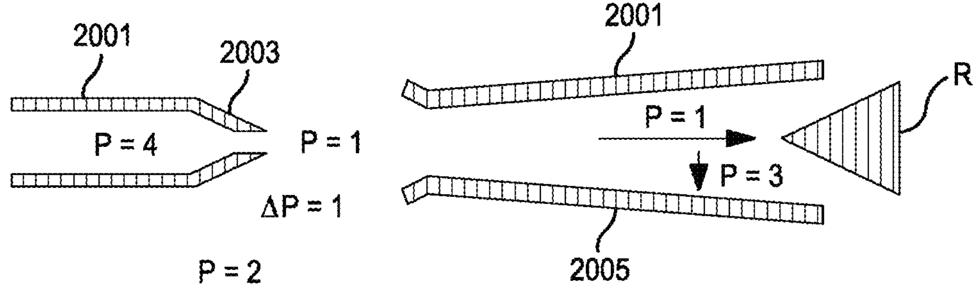
FIG. 20*b* is a schematic view of Venturi structure.

According to Venturi theories, when the delivery port of the Venturi meets resistance (Flow×Resistance=Pressure), pressure inside the Venturi body will increase, become ambient, and the flow entrainment will decrease (FIG. 20*b*). So, the flow volume delivery is inversely proportional to the pressure reached at the level of the airways; thus, when the system approaches the desired pressure level, the fraction of delivered gas comes almost exclusively from the high pressure pulsatile component.

Due to the Venturi effect, the flow delivered is converted into pressure (and vice versa) by adapting to the thoraco-pulmonary resistance. These factors permit the flow distribution to be optimized at the level of the airways, obverting preferential ventilation, and allowing the mean airway pressure to be kept relatively stable against the elastic and resistant forces of the respiratory structures.

In FIG. 20*a*, V1<V2>V3; and P1>P2<P3. In the zone of flow acceleration denoted by arrows Q and R, the pressure becomes sub ambient and gas is entrained. In FIG. 20*b*, when Resistance (R) is applied, the Venturi design delivers pressure with decreasing flow entrainment.

In FIG. 20*b*, the theoretical Venturi tube 2001 shows the pressure behaviors, according to the change in the tube geometry. When the diameter of the tube decreases at 2003, the velocity of the flow through the restriction will increase (Bernoulli effect), and according to the law of conservation of energy, pressure has to decrease, from 4 to 1, and become lower than the ambient pressure P=2, when entrainment will occur. By increasing the diameter of the tube at 2005, flow velocity will drop and consequently the pressure will recover. When resistance R is applied to the delivery port of the Venturi tube, the pressure inside the Venturi become sufficiently high, equalize with ambient, and decreasing the entrainment to zero.

Take FIGS. 19*a* and 19*b*, for example. In operation, when receiving high pressure pulsatile gas flow from the interrupter valve 11450, the Venturi body 1850 moves away from the resting position (open position, FIG. 19*b*); simultaneously gas passes through the stem passageway into the Venturi entrance 11451, creates a flow acceleration, and generates a lower than ambient pressure 11455, due to the Venturi effect. This encourages gas (from ambient, or from a low pressure circuit) to be entrained via 863 and enter into the Venturi. Because the Venturi tube has a bigger diameter as his delivery port 11456, flow will decelerate, recovers the pressure, and the subtidal volume is delivered to the patient airways. The sliding Venturi when driven to its maximal proximal position (occluded position), partially or fully obstructs the exhalation outlet port in order to reduce flow of exhalation gases (FIG. 19*a*). When the Venturi slider returns to the initial position (open position) after the applied pulse, the exhalation outlet port fully opens 854 allowing gases to escape (patient exhalation) (FIG. 19*b*). Each opening and closing represents one cycle (inspiration and expiration); thus, if a patient is ventilated at a rate of 100-300, or 600 cycles/min, that means that the Venturi will open and close 100-300, or 600 times/min.

Figure 21A:
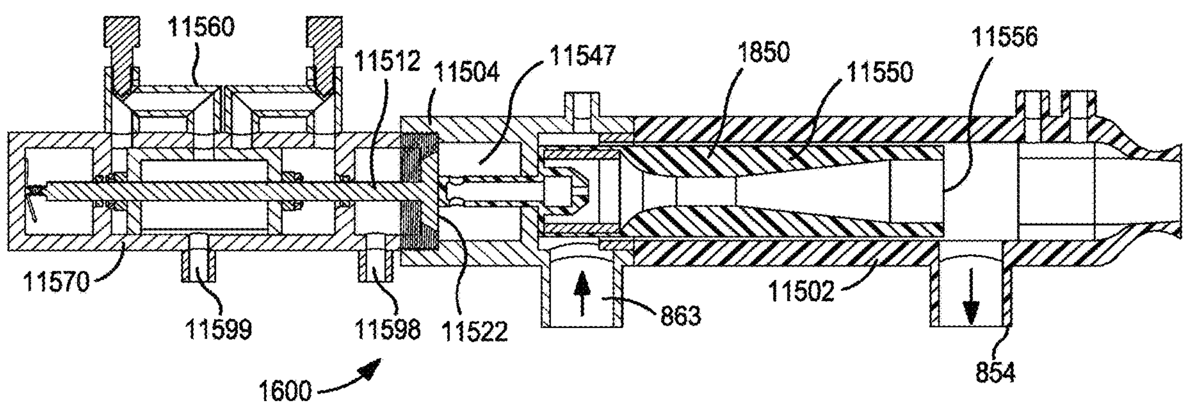
FIG. 21*a* is a schematic cross-section view of another embodiment of the Patient Interface Device according to the present invention.
Figure 21B:
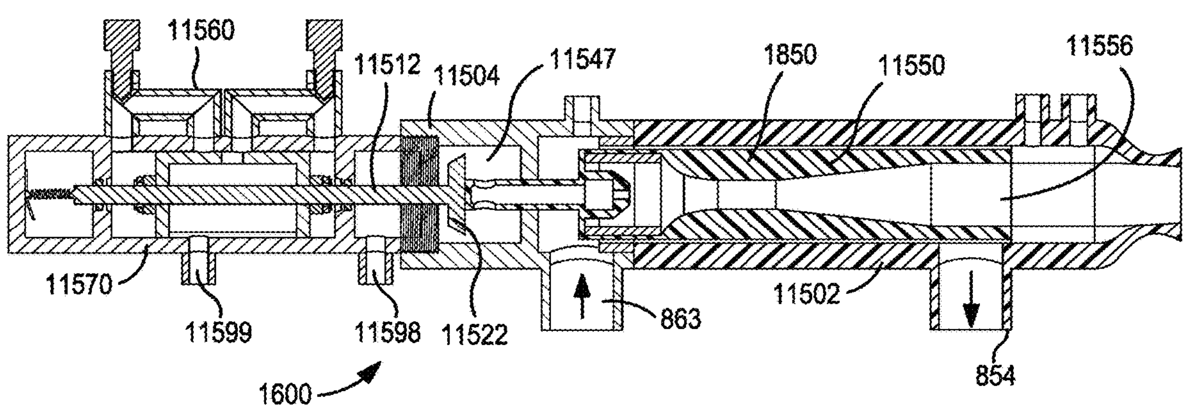
FIG. 21*b* is a schematic cross-section view of the another embodiment of the Patient Interface Unit according to the present invention.

FIGS. 21*a* and 21*b* show another Patient Interface Device 1600 embodiment, which is an extension of FIGS. 12*a* and 12*b*, in that it comprises a pneumatic bidirectional oscillating air-interrupter valve 11560 with a sliding Venturi shuttle 11550. Patient Interface Device 1600 may comprise a disposable part 11502 and reusable part 11504, similar to FIGS. 12*a* and 12*b*. The disposable part 11502 preferably comprises the slidable Venturi valve 1850, and the reusable part 11504 preferably employs a pneumatic double acting shuttle valve 11570. FIG. 20*a* shows a closed poppet valve 11522, and FIG. 20*b* shows an open poppet valve 11522—note both the shuttle valve 11570 and the sliding Venturi valve 1850 are connected (e.g., by welding the poppet valve 11522 with the jet tube) and move from side to side. Separate gas supplies 1598, 1599, respectively, are available for the patient supply and to operate the shuttle, if desired. Here, the oscillating shaft 11512 which supports the pneumatic shuttle valve 1850 is extended and fluidly communicates with the sliding Venturi shuttle 11550 from a feed chamber 11547. As the poppet valve 11522 opens in the manner described previously, the sliding shuttle 11550 moves synchronously. The same approach can be taken for the embodiments of FIGS. 10*a*, 10*b* or FIGS. 11*a*, 11*b*, respectively. In fact, the sliding Venturi acts as inspiratory, expiratory valves all in one. In addition, depending on the location of the outlet port 11556, the disposable shuttle body 11550 may be adapted so that the fully extended shuttle partially or fully occludes the expired air-port 854, increasing average positive airway pressure (PAP). In fact, the sliding Venturi acts as inspiratory, expiratory valves all in one.

Figure 22A:
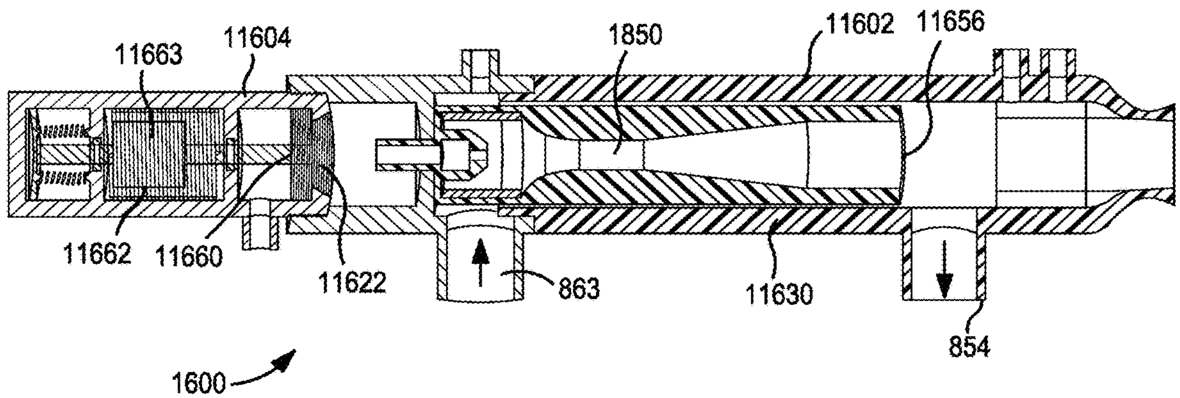
FIG. 22*a* is a schematic cross-section view of another embodiment of the Patient Interface Device according to the present invention.
Figure 22B:
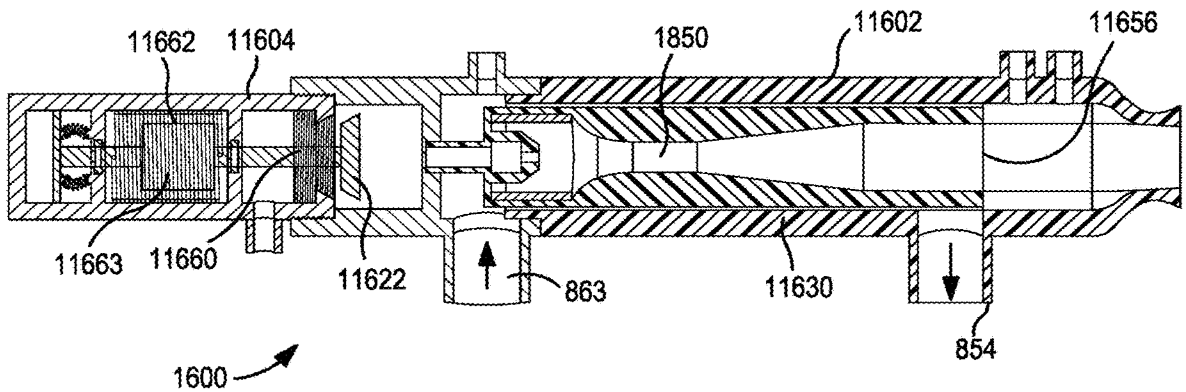
FIG. 22*b* is a schematic cross-section view of the another embodiment of the Patient Interface Unit according to the present invention.

FIGS. 22*a* and 22*b* show yet another Patient Interface Device 1600 combining the electromagnetic sliding valve principle of FIGS. 14*a* and 14*b*, together with the electromagnetic interrupter of features of FIGS. 10*a*, 10*b* and/or FIGS. 11*a*, 11*b*. Patient Interface Device 1600 comprises disposable part 11602 and reusable part 11604 as described above. The disposable part 11602 preferably comprises an electromagnetically activated sliding Venturi valve 1850, and the reusable part 11604 preferably employs an electromagnetically activated poppet valve 11622. FIG. 22*a* shows a closed poppet valve 11622, and FIG. 22*b* shows an open poppet valve 11622—note that both shuttle valve 11660 and the sliding Venturi valve 1850 may move independently. This embodiment provides maximum flexibility in the administering of Adaptive Dynamic Subtidal Ventilation pulses and the relative timing of the sliding Venturi valve 1850, as shown. The reusable part 11604 preferably comprises the solenoid interrupter valve 11662 and electromagnetic coils 11663. In an alternative similar to FIGS. 14*a* and 14*b*, coils may be clamped around the disposable part 11602, comprising the housing 11630 and the sliding Venturi valve 1850. In addition, depending on the location of the outlet port 11656, the disposable shuttle body 11602 may be adapted so that the fully extended shuttle partially or fully occludes the expired air-port 854, increasing average positive airway pressure (PAP). In fact, the sliding Venturi acts as inspiratory, expiratory valves all in one. A secondary solenoid may be employed to synchronously occlude the expired air-port 854, either fully or partially, to maximize the proximal patient PEP effect.

Figure 23A:
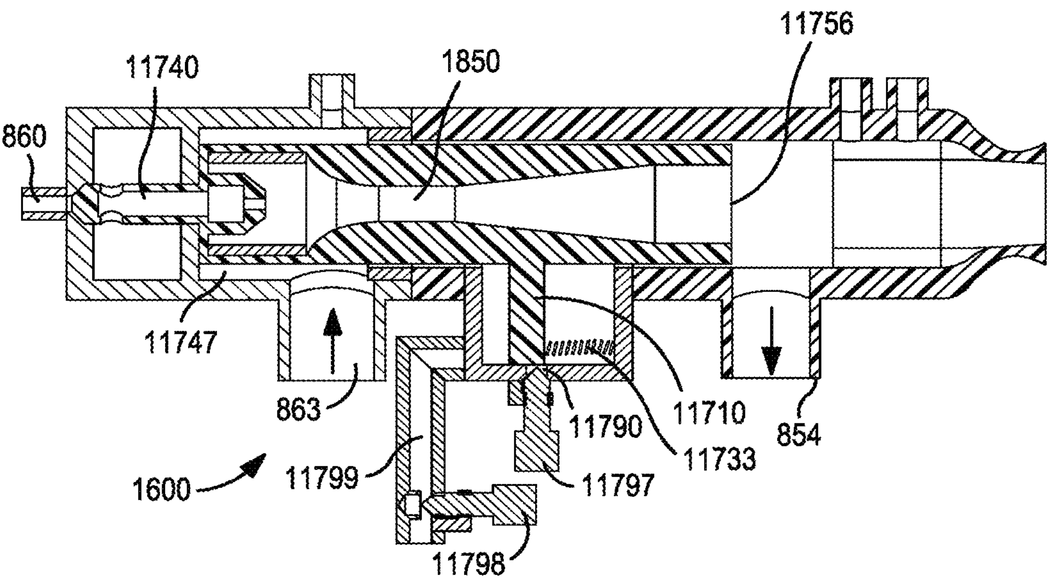
FIG. 23*a* is a schematic cross-section view of another embodiment of the Patient Interface Device according to the present invention.
Figure 23B:
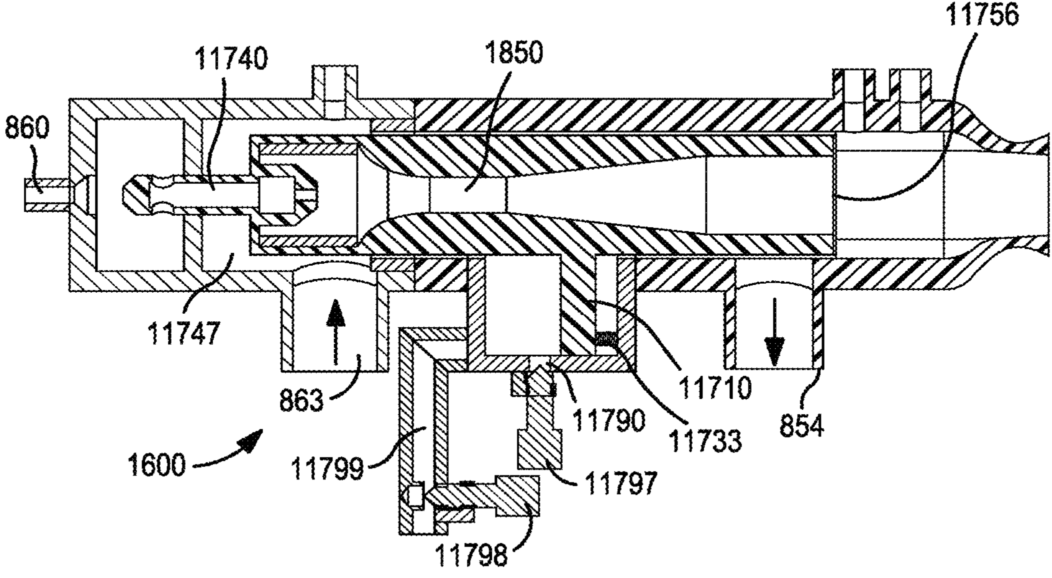
FIG. 23*b* is a schematic cross-section view of the another embodiment of the Patient Interface Unit according to the present invention.

Yet another embodiment of a compact, fully disposable Patient Interface Device 1600 is shown in FIGS. 23*a* and 23*b*. This embodiment combines a sliding Venturi valve 1850 operated by a movable shuttle 11710. Fully Disposable Patient Interface Device 1600 preferably comprises a sliding Venturi valve 1850 and a movable shuttle valve 11740 as a modification of FIGS. 17*a* and 17*b*. This approach is an extension of FIGS. 13*a* and 13*b*, where the movable shuttle 11710 now activates the sliding Venturi valve 1850 synchronously, employing a spring return 11733. The buckling spring 11733 provides non-linear effect wherein a predefined chamber 11747 pressure must be reached before the spring 11733 gives, then permitting the shuttle 11710 to abruptly slide. The vent 11790 is shown with a needle valve 11797 to alter a duty cycle, which would always be adjusted to flow greater than the inlet 11799 needle valve 11798, which controls frequency. A simplified approach may employ a fixed drilling for the vent. In addition, depending on the location of the outlet port 11756, the sliding Venturi valve 1850 will be able to partially or fully occlude the expired air-port 854, increasing average positive airway pressure (PAP). In fact, the sliding Venturi acts as inspiratory, expiratory valves all in one.

Figure 24A:
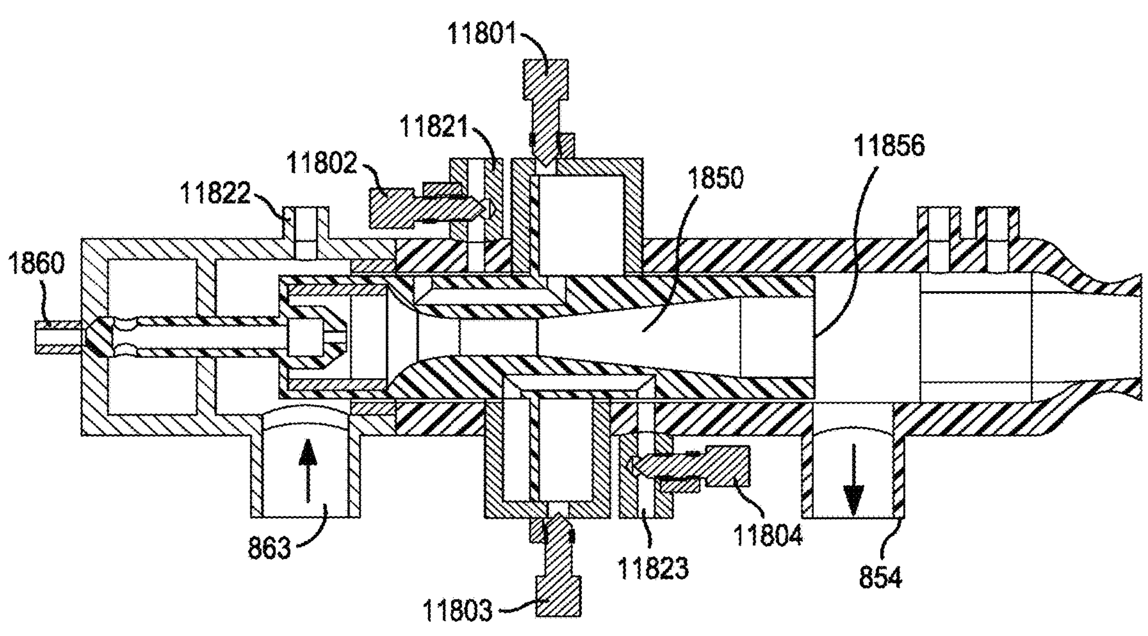
FIG. 24*a* is a schematic cross-section view of another embodiment of the Patient Interface Device according to the present invention.
Figure 24B:
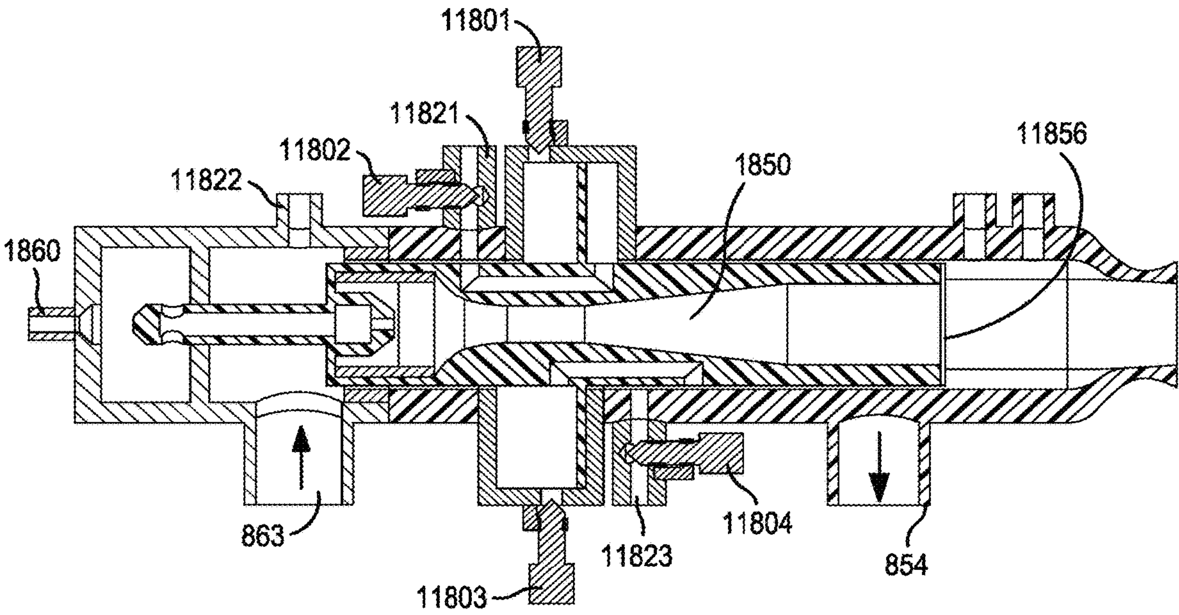
FIG. 24*b* is a schematic cross-section view of the another embodiment of the Patient Interface Unit according to the present invention.

FIGS. 24*a* and 24*b* show an additional preferred embodiment which employs a double action to forcibly return the slidable Venturi valve 1850, and does not rely on spring pressure alone. The double acting pneumatic slidable Venturi valve 1850 preferably employs four needle valves 11801, 11802, 11803, 11804 for maximum flexibility in configuration, and up to three gas inlets 11821, 1860, 11823. The first gas inlet 860 is for the patient, and may be air, $O_2$, or a combination at an optimum therapeutic pressure. The second gas inlet 11821 is to slide the Venturi valve 1850 towards the patient, and employs two needle valves 11801, 11802—one to control the buildup of pressure and to slide the Venturi, and the other one to vent. The third gas inlet 11823, which may be different pressure from the first and second inlets, also has two needle valves 11803, 11804 to control the rate of pressure rise to return the sliding Venturi valve 1850 back home, and to vent. The four needle valves and differing pressures permit precise control of frequency and duty cycle. A simpler double acting sliding Venturi valve embodiment may have a single gas supply to both the patient and actuators, and employs a single needle valve to control frequency, with fixed drillings in place of the other needle valves to set the duty cycle, or variations there between. In addition, depending on the location of the outlet port 11856, the sliding Venturi valve 1850 will be able to partially or fully occludes the expired air-port 854, increasing average positive airway pressure (PAP). In fact, the sliding Venturi acts as inspiratory, expiratory valves all in one.

Figure 25:
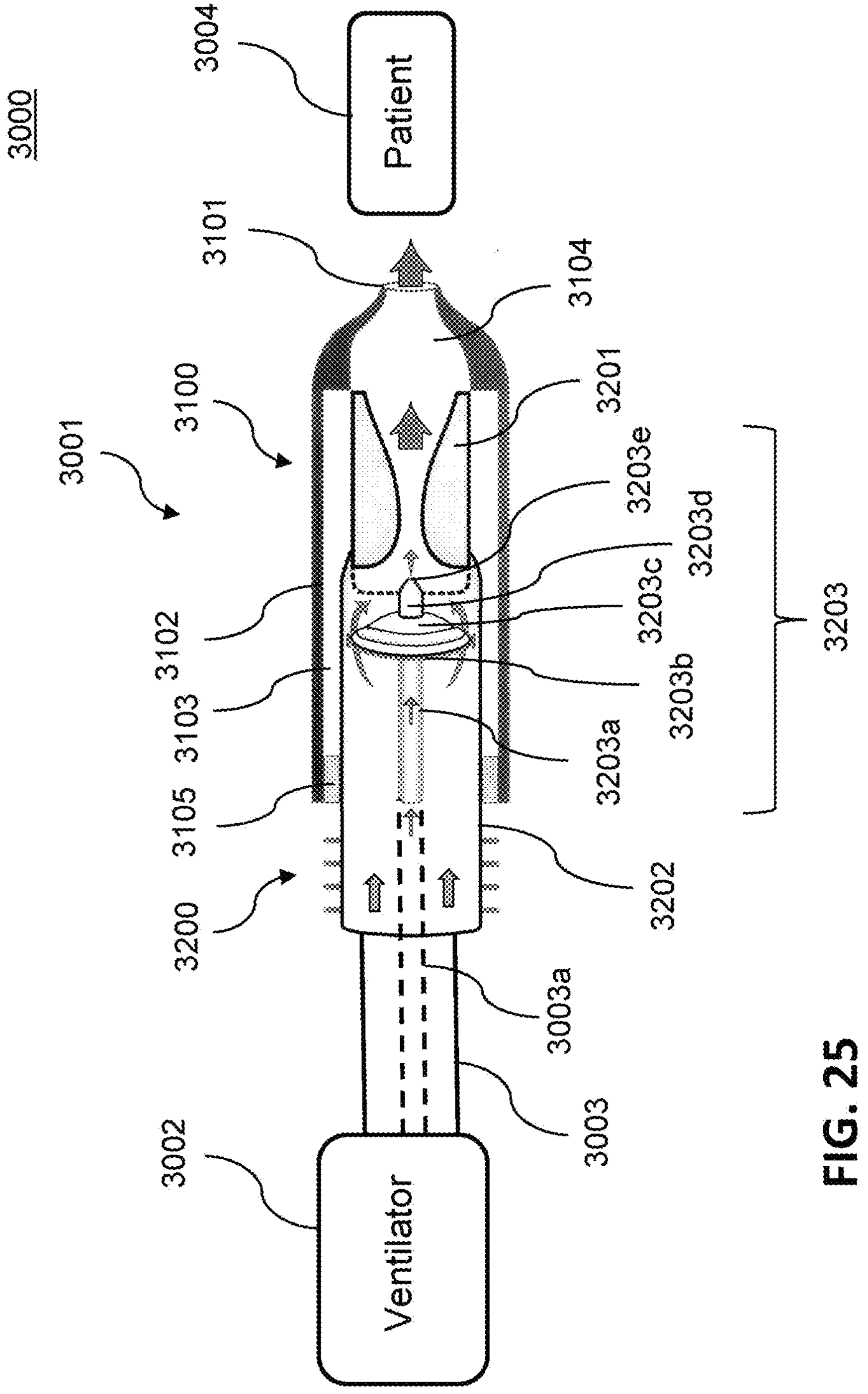
FIG. 25 is a diagram illustrating a ventilation system which includes Patient Interface Device of the disclosed invention.
Figure 26A:
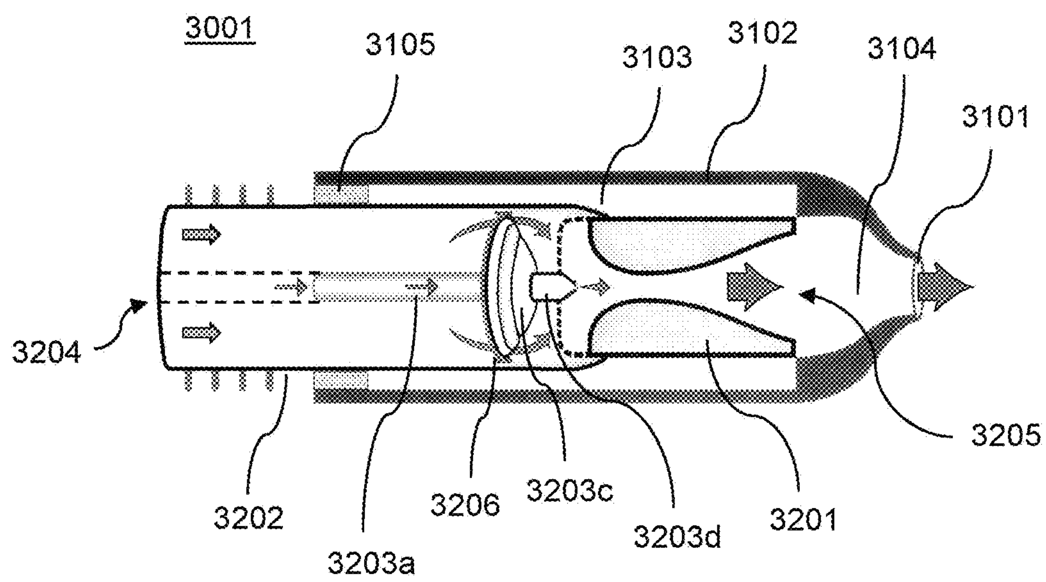
FIGS. 26*a*-26*b* are schematic cross-sectional views of the Patient Interface Device illustrating configurations of the Patient Interface Device during inspiratory phase and expiratory phase, respectively.
Figure 26B:
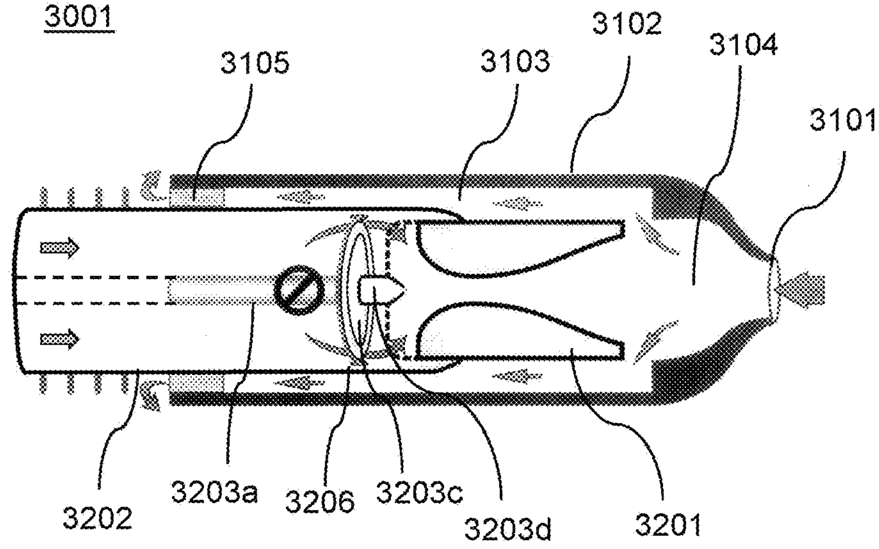

With reference to FIG. 25, shown is a diagram illustrating a ventilation system 3000 which includes patient interface device 3001 of the disclosed invention. With reference to FIGS. 26*a*-26*b*, shown are cross-sectional views of patient interface device 3001 of an embodiment of the disclosed invention. FIG. 26*a* illustrates a configuration of the patient interface device 3001 in pressurized closed position during sub-tidal ventilation inspiratory phase, and FIG. 26*b* illustrates a configuration of the patient interface device 3001 in unpressurized open position during sub-tidal ventilation expiratory phase. The patient interface device 3001 may be used for a breathing circuit for a ventilation system 3000, and may be used with the Adaptive Dynamic Subtidal Ventilation (ADSV) technology which is described above.

Referring to FIGS. 25, 26*a* and 26*b*, the ventilation system 3000 includes patient interface device 3001, ventilator 3002, and tubing system 3003 that connects the patient interface device 3001 to the ventilator 3002. The patient interface device 3001 has patient connection orifice 3101 that supplies inhalation gas to patient 3004 and receives exhalation gas from the patient 3004. The ventilator 3002 may supply pressurized gas to the patient interface device 3001. The tubing system 3003 includes at least one flexible tube such as a corrugated respiratory tube to deliver pressurized gas to the patient interface device 3001. The tubing system 3003 may include additional tubes and wires.

The patient interface device 3001 includes expiration module 3100 and inspiration module 3200. The inspiration module 3200 is constructed to receive pressurized gas from the ventilator 3002 and to deliver the pressurized gas to the patient 3004 during an inspiratory phase. The expiration module 3100 is constructed to vent exhalation gas from the patient 3004 during an expiratory phase. The inspiratory phase refers to the process or period in which the patient inhales gas through the patient interface device 3001, and the expiratory phase refers to the process or period in which the patient exhales gas into the patient interface device 3001.

The expiration module 3100 includes hollow outer body 3102 that partially encloses the inspiration module 3200. The expiration module 3100 includes exhalation channel 3103 through which exhalation gas from the patient is vented to the ambient or other external systems. The exhalation channel 3103 may be a space between a wall of the hollow outer body 3102 and the inspiration module 3200. Alternatively, the exhalation channel 3103 may include one or more channels or tubes formed in the outer body 3102 to vent the exhalation gas from the patient. The expiration module 3100 may include one or more filters 3105 that are disposed in the exhalation channel 3103. The expiration module 3100 has patient connection orifice 3101 that is formed at an end of the expiration module 3100, forming a gas flow path between internal space 3104 of the outer body 3102 and the patient 3004. Through the patient connection orifice 3101, inhalation gas is supplied to patient 3004 during the inspiratory phase and exhalation gas is received from the patient 3004 during the expiratory phase.

The inspiration module 3200 includes hollow inner body 3202 and sliding Venturi valve 3201 slideably mounted inside the inner body 3202. The inner body 3202 is partially disposed inside the hollow outer body 3102 so that a space between the inner body 3202 and the outer body 3102 may work as an exhalation channel 3103. The inspiration module 3200 has at least one inlet port 3204 connected to the tubing system 3003 to receive pressurized gas and outlet port 3205 to exhaust the pressurized gas into the internal space 3104. The outlet port 3205 of the inspiration module 3200 may be an opening at an end of the sliding Venturi valve 3201 toward the patient connection orifice 3101. The inspiration module 3200 includes high pressure flow unit 3203 that is disposed inside the inner body 3202 and delivers high pressure gas flow to the sliding Venturi valve 3201. The high pressure flow unit 3203 includes high pressure flow tube 3203*a* having cap 3203*b* at an end, servo diaphragm 3203*c* coupled to the cap 3203*b*, and jet 3203*d* connected to the servo diaphragm 3203*c* and the sliding Venturi valve 3201. The jet 3203*d* has jet orifice 3203*e* through which the pressurized gas flows into the Venturi valve 3201. While the sliding Venturi valve 3201 slides in a first or second direction, the jet 3203*d* pulls or presses the diaphragm 3203*c* which opens or closes the high pressure flow tube 3203*a*. The sliding Venturi valve 3201 is configured to slide in a first direction (toward the patient connection orifice 3101) to open the high pressure flow tube 3203*a* and to close the exhalation channel 3103 during the inspiratory phase (FIG. 26*a*) and to slide in a second direction (toward the high pressure flow unit 3203) to close the high pressure flow tube 3203*a* and to open the exhalation channel 3103 during the expiratory phase (FIG. 26*b*).

The ventilator 3002 is connected to the patient interface 3001 by the tubing system 3003 that self contains tube 3003*a* that delivers high pressure pulsatile dry gas to the sliding Venturi 3201. The tube 3003*a* of the tubing system 3003 is connected to the high pressure flow tube 3203*a* of the high pressure flow unit 3203 to supply the high pressure pulsatile dry gas to the high pressure flow tube 3203*a*. Optionally, the tubing system 3003 may include a wired (for heating) corrugated respiratory tube (not shown) that may indirectly heat the high pressure flow tube 3203*a* and affect the temperature of the high pressure pulsatile gas.

The inspiration module 3200 is constructed to have a bias flow channel 3206 between the high pressure flow unit 3203 and the wall of the hollow inner body 3202. The tubing system 3003 may further deliver to the inner body 3202 a bias flow of humidified and eventually heated gas that may be entrained by Venturi effect at each pulse generated at the jet orifice 3203*e*. The bias flow may compensate the dryness of the high pressure pulsatile gas flow. The subtidal volume of gas delivered to the patient at each inspiration may be a mixture of an high pressure pulsatile gas and an low pressure bias flow. The bias flow channel 3206 is open to the sliding Venturi valve 3201 during inspiratory and expiratory phases, as shown in FIGS. 26*a*-26*b*. The tubing system 3003 may include additional channels or tubes to deliver the bias gas flow from the ventilator 3002 or from external sources.

During subtidal volume delivery, the fraction of the bias flow will vary at each inspiration depending on the change in the patient airways resistance and compliance. The bias flow may provide similar benefits and utilities as described above for the embodiments referring to FIGS. 17*a*-18*b*. During ADSV technology ventilation, the pulsatile flow size/amplitude may be operator dependent, while the amount of the bias flow in each subtidal volume delivered may depend on the patient's airway characteristics such as resistance "R" compliance (see FIG. 20*b*). Consequently, when the compliance decreases (low lung volume and "R" is high), bias flow entrainment drops and the amount of flow to the patient drops too, which prevents the patient's airway from being overwhelmed by the flow as there is no more space for a large volume of flow. When the compliance increases (better lung volume and "R" drops), bias flow entrainment may increase and the amount of flow to the patient may increase too to fill the available new space and accommodate the lungs. The percentage of the bias flow relative to the total delivered subtidal volume may be different at each inspiration to accommodate the patient's airways and prevent lung trauma and thus thanks to the Venturi effects.

In the inspiratory phase, the Venturi valve 3201 slides toward the patient connection orifice 3101 to the first position (pressurized closed position) as shown in FIG. 26*a*, blocking the path from the inner space 3104 to the exhalation channel 3103, and pulls the servo diaphragm 3203*c* so that the high pressure flow tube 3203*a* is open to the jet 3203*d* delivering the pressurized gas to the Venturi valve 3201. The pressurized gas received through the inlet port 3204 flows to the patient 3004 through the high pressure flow tube 3203*a*, jet 3203*d*, sliding Venturi valve 3201, and the patient connection orifice 3101. See arrows in FIG. 26*a*.

In the expiratory phase, the Venturi valve 3201 moves toward the high pressure flow unit 3203 to the second position (unpressurized open position) as shown in FIG. 26*b*, opening the path between the exhalation channel 3103 and the inner space 3104, and presses the diaphragm 3203*c* so that the path between the high pressure flow tube 3203*a* and the jet 3203*d* is closed. In this state, there is no gas flow through the high pressure flow tube 3203*a*. The exhalation gas from the patient 3004 flows to the ambient or external devices through the inner space 3104 and the exhalation channel 3103. See arrows in FIG. 26*b*.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions. The individual components shown in outline or designated by blocks in the attached Drawings are all well-known in the patient ventilation arts, and their specific construction and operation are not critical to the operation or best mode for carrying out the invention.

All U.S. and foreign patents and patent applications discussed above are hereby incorporated by reference into the Detailed Description of the Preferred Embodiments.

What is claimed is:

1. A patient interface device for delivering percussive gas to a patient, comprising:

an inspiration module having at least one inlet port to receive pressurized gas and an outlet port to deliver the pressurized gas to the patient during inspiratory phase, wherein the inspiration module comprises a hollow inner body and a sliding Venturi valve slidably connected to the inner body, wherein the Venturi valve is configured to slide relative to the inner body; and an expiration module comprising a hollow outer body that partially encloses the inner body of the inspiration module and completely encloses the sliding Venturi valve, wherein the expiration module is configured to vent exhalation gas from the patient during expiratory phase and wherein the exhalation module includes a patient connection orifice to deliver the pressurized gas to the patient and to receive the exhalation gas from the patient.

2. The patient interface device of claim 1 wherein an exhalation channel is formed in the outer body to vent the exhalation gas from the patient during the expiratory phase.

3. The patient interface device of claim 1 wherein the inspiration module comprises a high pressure flow unit that is disposed inside the inner body and comprises:

a tube for receiving the pressurized gas;

a servo diaphragm coupled to an end of the tube; and a jet connected to the servo diaphragm and to the sliding Venturi valve.

4. The patient interface device of claim 3 wherein the sliding Venturi valve is configured to slide in a direction while pulling the jet and the servo diaphragm to open the tube during the inspiratory phase and is configured to slide in an opposite direction while pressing the jet and the servo diaphragm to close the tube during the expiratory phase.

5. The patient interface device of claim 4 wherein the high pressure flow unit is configured such that the pressurized gas received through the inlet port flows through the tube, the jet and the sliding Venturi valve when the diaphragm is pulled.

6. The patient interface device of claim 3 wherein the inspiration module is configured to include a bias flow channel formed between the high pressure flow unit and a wall of the hollow inner body, and wherein the bias flow channel is configured to provide a bias gas flow to the sliding Venturi valve.

7. The patient interface device of claim 6 wherein the bias gas flow is a flow of humidified gas and the pressurized gas supplied to the tube is pressured pulsatile dry gas.

8. The patient interface device of claim 1 wherein an exhalation channel is formed between a wall of the hollow outer body and the inner body, and is configured to vent the exhalation gas from the patient therethrough during the expiratory phase.

9. The patient interface device of claim 8 wherein the sliding Venturi valve is configured to be at a first position to close the exhalation channel during the inspiratory phase and to be at a second position to open the exhalation channel during the expiratory phase.

10. A ventilation system for delivering percussive gas to a patient, comprising:

a ventilator that is configured to supply pressurized gas;

a patient interface device for delivering percussive gas to the patient, comprising:

an inspiration module having at least one inlet port to receive pressurized gas and an outlet port to deliver the pressurized gas to the patient during inspiratory phase, wherein the inspiration module comprises a hollow inner body and a sliding Venturi valve slidably connected to the inner body, wherein the Venturi valve is configured to slide relative to the inner body; and an expiration module comprising a hollow outer body that partially encloses the inner body of the inspiration module and completely encloses the sliding Venturi valve, wherein the expiration module is configured to vent exhalation gas from the patient during expiratory phase and wherein the exhalation module includes a patient connection orifice to deliver the pressurized gas to the patient and to receive the exhalation gas from the patient; and a tubing system including at least one flexible tube connecting the ventilator to the patient interface device.

11. The ventilation system of claim 10 wherein an exhalation channel is formed in the outer body to vent the exhalation gas from the patient during the expiratory phase.

12. The ventilation system of claim 10 wherein the inspiration module comprises a high pressure flow unit that is disposed inside the inner body and comprises:

a tube for receiving the pressurized gas;

a servo diaphragm coupled to an end of the tube; and a jet connected to the servo diaphragm and to the sliding Venturi valve.

13. The ventilation system of claim 12 wherein the sliding Venturi valve is configured to slide in a direction while pulling the jet and the servo diaphragm to open the tube during the inspiratory phase and is configured to slide in an opposite direction while pressing the jet and the servo diaphragm to close the tube during the expiratory phase.

14. The ventilation system of claim 13 wherein the high pressure flow unit is configured such that the pressurized gas received through the inlet port flows through the tube, the jet and the sliding Venturi valve when the diaphragm is pulled.

15. The ventilation system of claim 12 wherein the inspiration module is configured to include a bias flow channel formed between the high pressure flow unit and a wall of the hollow inner body, and wherein the bias flow channel is configured to provide a bias gas flow to the sliding Venturi valve.

16. The ventilation system of claim 15 wherein the bias gas flow is a flow of humidified gas and the pressurized gas supplied to the tube is pressured pulsatile dry gas.

17. The ventilation system of claim 15 wherein the tubing system includes at least one channel to deliver the bias gas flow to the inspiration module.

18. The ventilation system of claim 10 wherein an exhalation channel is formed between a wall of the hollow outer body and the inner body, and is configured to vent the exhalation gas from the patient therethrough during the expiratory phase.

19. The ventilation system of claim 18 wherein the sliding Venturi valve is configured to be at a first position to close the exhalation channel during the inspiratory phase and to be at a second position to open the exhalation channel during the expiratory phase.

* * * * *